(12) United States Patent
Baid

(10) Patent No.: US 11,524,145 B2
(45) Date of Patent: Dec. 13, 2022

(54) FLUID ADMINISTRATION MEDICAL APPARATUS AND INTRAVENOUS CATHETER ASSEMBLY

(71) Applicant: POLY MEDICURE LIMITED, Faridabad (IN)

(72) Inventor: Rishi Baid, New Dehli (IN)

(73) Assignee: POLY MEDICURE LIMITED, Faridabad (IN)

( * ) Notice: Subject to any disclaimer, the term of this patent is extended or adjusted under 35 U.S.C. 154(b) by 404 days.

(21) Appl. No.: 16/473,244

(22) PCT Filed: Mar. 23, 2018

(86) PCT No.: PCT/IB2018/051974
§ 371 (c)(1),
(2) Date: Jun. 24, 2019

(87) PCT Pub. No.: WO2018/172985
PCT Pub. Date: Sep. 27, 2018

(65) Prior Publication Data
US 2020/0139088 A1     May 7, 2020

(30) Foreign Application Priority Data

Mar. 24, 2017 (IN) .............................. 201711010513

(51) Int. Cl.
*A61M 25/06* (2006.01)
*A61M 25/00* (2006.01)

(52) U.S. Cl.
CPC .... *A61M 25/0625* (2013.01); *A61M 25/0097* (2013.01); *A61M 25/0606* (2013.01); *A61M 25/0693* (2013.01)

(58) Field of Classification Search
CPC ............ A61M 25/0618; A61M 39/045; A61M 39/06; A61M 2039/064; A61M 2039/066;
(Continued)

(56) References Cited

U.S. PATENT DOCUMENTS

| 4,387,879 A | * | 6/1983 | Tauschinski | ...... A61M 39/0693 604/249 |
| 5,613,956 A | * | 3/1997 | Patterson | .......... A61M 39/0606 604/167.04 |

(Continued)

FOREIGN PATENT DOCUMENTS

| EP | 2022421 A1 | 2/2009 |
| EP | 2049183 A1 | 4/2009 |

(Continued)

OTHER PUBLICATIONS

International Search Report issued for corresponding International Patent Application No. PCT/IB2018/051974 dated May 24, 2018.
(Continued)

*Primary Examiner* — Theodore J Stigell
*Assistant Examiner* — Rachel T. Smith
(74) *Attorney, Agent, or Firm* — Moore & Van Allen PLLC; Henry B. Ward, III

(57) ABSTRACT

An apparatus comprising a catheter tube; a hub having a distal section joined to the catheter tube and a proximal section defining a housing; at least one port connected to the hub by a fluid passage through a passageway; a needle extending through the hub and the catheter tube, wherein the needle has opposite proximal and distal ends, the distal end forming a needle tip; a needle hub attached to the proximal end of the needle; a needle guard slidably arranged on the needle, wherein the needle guard is movably retained in the housing of the hub when the needle extends through the hub and the catheter tube, wherein the needle guard is removable from the hub once the needle tip is received in the needle guard upon withdrawal of the needle from the catheter tube; and wherein the hub is made of two parts each having distal and proximal end sections.

19 Claims, 13 Drawing Sheets

(58) Field of Classification Search
CPC ...... A61M 2039/0686; A61M 25/0625; A61M 25/0097; A61M 25/0606; A61M 25/0693; A61M 25/0637; A61M 25/0612
See application file for complete search history.

(56) References Cited

U.S. PATENT DOCUMENTS

| | | | |
|---|---|---|---|
| 7,465,286 B2 | 12/2008 | Patterson et al. | |
| 8,147,424 B2 | 4/2012 | Kassab et al. | |
| 2011/0245800 A1 | 10/2011 | Kassab et al. | |
| 2012/0271235 A1* | 10/2012 | Fuchs | A61M 5/158 604/164.08 |
| 2013/0237925 A1 | 9/2013 | Trainer et al. | |
| 2015/0202422 A1 | 7/2015 | Ma et al. | |
| 2015/0306349 A1* | 10/2015 | Bonnal | A61M 25/0097 604/272 |
| 2015/0328438 A1 | 11/2015 | Baid | |
| 2016/0106959 A1* | 4/2016 | Woehr | A61M 5/36 604/125 |
| 2016/0206834 A1* | 7/2016 | Shluzas | A61M 5/3293 |
| 2016/0331937 A1 | 11/2016 | Teoh | |
| 2016/0361490 A1* | 12/2016 | Phang | A61M 25/0625 |
| 2018/0200487 A1* | 7/2018 | Sokolski | A61M 5/326 |
| 2018/0214682 A1* | 8/2018 | Woehr | A61M 39/0247 |

FOREIGN PATENT DOCUMENTS

| | | |
|---|---|---|
| EP | 3131614 A1 | 2/2017 |
| JP | 2016005806 A | 1/2016 |
| WO | WO-2017151052 A1 * | 9/2017 |

OTHER PUBLICATIONS

Written Opinion issued for corresponding International Patent Application No. PCT/IB2018/051974 dated May 24, 2018.
First Examination Report issued by the Indian Patent Office for Indian Patent Application No. 201711010513, dated Mar. 17, 2021.
Extended Search Report issued by the European Patent Office for European Patent Application No. 21187637.0, dated Nov. 23, 2021.
Extended Search Report issued by the European Patent Office for European Patent Application No. 21187617.2, dated Nov. 12, 2021.

* cited by examiner

FLUID ADMINISTRATION MEDICAL APPARATUS AND INTRAVENOUS CATHETER ASSEMBLY

FIELD OF THE INVENTION

The invention generally relates to fluid administration or infusion apparatus. The invention also relates to intravenous catheter assemblies. More particularly, the invention relates to a fluid administration medical apparatus comprising a hub arranged at a proximal end of a catheter tube and having an inner surface defining a housing; a needle having a needle tip and extending through the housing and the catheter tube when in a ready position; and a needle guard slidably arranged on the needle and received in the housing when the needle is in its ready position, wherein the needle guard is configured to guard the needle tip upon withdrawal of the needle from the hub.

BACKGROUND OF THE INVENTION

A fluid administration medical apparatus and intravenous catheter assembly of the aforementioned kind is generally known by the person skilled in the art and might be used for infusion as well as transfusion purposes. Such fluid administration medical apparatus generally includes a catheter hub carrying a catheter and a removable needle cannula extending through the catheter and past the distal tip of the catheter for inserting the needle and catheter through the skin and into a vein of a patient. Once the venipuncture is successfully performed, the needle is detached and a source of infusion liquid, such as glucose, saline solution, blood or other fluid is connected to the catheter hub to supply the infusion fluid to the vein of the patient.

Healthcare workers are increasingly at risk of disease transmission, and nurses perform most of invasive hypodermic procedures, such as injecting medicine, collecting blood and inserting indwelling intravenous (I.V.) catheters. Nurses and other healthcare personnel are routinely injured by the exposed, sharp lancet of the needle after use on a patient. For example, splattered blood could enter a mucous membrane region of the eyes, nose or mouth of any healthcare personnel within proximity to the splatter. The exposure should then be reported and post exposure treatment, prophylaxis and follow up would occur, incurring costs to the institution and worry to the individual exposed to the blood.

Carrying out the above steps without bringing in air into the system is relatively tedious and involves a sufficient amount of skill and generally results in blood leaking from the apparatus and soiling clothing or the like or requiring the use of absorbent materials to catch the escaping blood. Also, the above connection of the infusion liquid source to the apparatus requires manipulation of parts while the catheter is in the vein of the patient, and this tends to increase patient discomfort and the danger of damage to the patient.

Moreover, such apparatuses are available without any safety features preventing needle stick injury. Typically, needle guard serves to automatically cover the needle tip after withdrawal of the needle, for example, from a patient. Such needle guard serves to prevent accidental pricking of, for example, a medical practitioner by the needle tip after removal of the needle from the medical apparatuses. Thus, the needle can be safely disposed of after use, without the danger of transmitting possible highly infectious and/or deadly diseases to the medical practitioner.

It is desired to provide a fluid administration medical apparatus with improved safety features having a needle guard slidably arranged on the needle and received in the hub when the needle is in its ready position, wherein the needle guard is configured to guard the needle tip upon withdrawal of the needle from the hub.

Further, the apparatuses of prior art have drawbacks including that their design also imposes significant drag force on the needle shaft, which make them difficult and undesirable to use and causes pain to the patient when in use. Generally, when the needle is withdrawn from a patient, the needle grates or otherwise causes friction or creates a drag as it slides through catheter, the hub or through needle guard creating drag or a withdrawal force.

Another disadvantage of the prior art apparatuses is not only that they are complicated or assembled of a large number of parts, but also that they possess risks of not working properly and that high manufacturing costs are involved in producing each of the parts and in assembling them.

A further disadvantage is that extra operations are necessary to operate the apparatus which possess risk of omissions or wrongly executed operations by the operator.

Hence, there is a requirement for a low-cost medical apparatus with a universal application which shall prevent accidental contact of a medical professional or any other person with the sharp tip of the needle after use of the disposable medical apparatus and thus prevent possible transmission of an infectious disease such as hepatitis, HIV, etc.

It is also desired to provide a fluid administration medical apparatus that significantly decrease the withdrawal force required and friction caused as a needle is withdrawn through a hub being protected by a needle guard.

Catheter assemblies are used to place a catheter properly into the vascular system of a patient. Once in place, catheters such as intravenous ("IV") catheters may be used to infuse fluids including normal saline, medicinal compounds, and/or nutritional compositions or the like into a patient in need of such treatment. Catheters additionally enable the removal of fluids from the circulatory system and monitoring of conditions within the vascular system of the patient.

One type of commonly used catheter is a peripheral intravenous catheter which are indwelling intravenous catheters often used to provide an entry route for medications, fluid for hydration, and in some cases, for parenteral feeding, into a patient. Such catheters are generally short in length, ranging from about one-half to about three inches in length, and are generally made of flexible biocompatible materials. Peripheral intravenous catheters are often provided as "over-the-needle" catheters mounted over an introducer needle with a sharp distal tip. A portion of the catheter including at least the distal tip of the catheter securely grips the outside of the needle to prevent catheter peelback during insertion of the catheter into the circulatory system of the patient. Although several techniques for placing such catheters are practiced in the art, many generally include the step of inserting at least a portion of the needle into the target vessel and then sliding the catheter over the needle into place.

Once placement of the needle has been confirmed, the medical personnel may remove the needle, leaving the catheter in place. A septum within the catheter housing can prevent the outflow of fluid during and following removal of the introducer needle. These septum structures are generally elastomeric and are designed to closely conform to the shape of a needle during storage and use to prevent leaking, then to seal upon removal of the needle. However, if the needle is left within the septum for long periods, the septum may not completely seal after the needle is removed, having conformed, in part, to the shape of the withdrawn needle. An incompletely sealed septum can increase the risk of blood exposure to medical personnel, since blood may flow through the small opening in the slit of the septum. It would thus be an improvement in the art to provide a catheter assembly with more reliable sealing functionality. Such a catheter assembly is disclosed herein.

The catheter assembly is also provided with a needle guard slidably arranged on the needle and received in the housing when the needle is in its ready position, wherein the needle guard is configured to guard the needle tip upon withdrawal of the needle from the catheter hub.

The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

According to one of the embodiments of the invention, the catheter hub and/or needle hub within which the needle guard is received in a ready position includes holding mechanisms for holding the needle guard even under retracting forces acting on the needle guard when the needle is retracted out of the patient's vein. These holding mechanisms may include one or more depressions formed on the inner circumferential surface of the catheter hub and/or needle hub into which one or more protrusions formed on the first and second arm of the needle guard securely engages in the ready position. For example, when the first arm is deflected and spread apart from the second arm by the needle shaft.

SUMMARY AND OBJECTS OF THE INVENTION

A primary object of the present invention is to provide a fluid administration medical apparatus with improved safety features wherein the above shortcomings are significantly prevented.

Another object of the present invention is to provide an improved fluid administration medical apparatus with safety features having a needle guard slidably arranged on the needle and received in the housing when the needle is in its ready position, wherein the needle guard is configured to guard the needle tip upon withdrawal of the needle from the hub.

Another object of the present invention is to provide an improved fluid administration medical apparatus that significantly decrease the withdrawal force required and friction caused as a needle is withdrawn through a hub being protected by a needle guard.

Yet another object of the present invention is to provide an improved fluid administration medical apparatus which is inexpensive to manufacture, efficient, effective and simple in its construction and use.

Yet another primary object and advantage of the present invention is to provide an improved intravenous catheter assembly which is inexpensive to manufacture, efficient, effective and simple in its construction and use.

It is another object of the present invention to provide an intravenous catheter assembly which provides better protection against accidental pricking by the needle tip and which is inexpensive to manufacture at the same time.

It is another object of the present invention to provide an intravenous catheter assembly with improved safety features having a needle guard slidably arranged on the needle and received in the hub when the needle is in its ready position, wherein the needle guard is configured to guard the needle tip upon withdrawal of the needle from the hub.

It is another object of the present invention to provide an intravenous catheter assembly which has better blood control features.

It is another object of the present invention to provide a compact design for housing one or more valves within the catheter hub housing of the intravenous catheter assembly having better blood control features.

The needle guard of the present invention includes a base portion made of a first material and having a needle passage which extends in an axial direction from a proximal side of the base portion through the base portion to a distal side of the base portion, such that a needle having a principal outer profile can be movably arranged in the needle passage. The needle guard further includes first and second arms extending substantially in the axial direction from the distal side of the base portion, with the first arm having a distal region and a proximal region. A distal wall is transversely arranged in the distal region of the first arm. The arms may be resilient. A distal wall may also be transversely arranged in the distal region of the second arm. The length of the distal wall can be adjusted according to requirements, i.e., it can be long enough to cover the first and/or second arm or go beyond the first or second arms in the protected position. Likewise, the width and the height of the distal wall can be longer than the width and the height of the distal wall of the second arm. The distal wall may have flaps on the side or on the base of the distal wall to ensure that the needle tip does not slide out from the side or bottom of the distal wall either due to pivoting of the needle or due to any external forces. The distal wall has side edges/faces and bottom edges and faces.

The distal wall may be made of a resilient material which is different from the material with which the needle guard is made up of to prevent the penetration of the distal wall by the needle tip.

The needle guard may also have retaining mechanisms to attach to the inside or outside of the second part catheter hub. These retaining mechanisms can be places anywhere along the needle guard wherein the retaining mechanisms may be present on the base portion of anywhere along the first or second arms. There may be more than one retaining mechanisms on the needle guard. In some embodiments the tensioning element acts as a retaining mechanism for holding the needle guard inside the catheter hub until the needle tip is safely within the needle guard. The tensioning element may hold the needle guard inside the catheter hub by friction or tight fit due to being stretched out by the first and/or second arms. Once the needle tip is inside the needle guard, the resilient arms snap down and the tensioning element is released from the retaining relation with the catheter hub, thus allowing the needle guard to be removed from the catheter hub.

Accordingly, the present invention relates to a fluid administration medical apparatus comprising: a catheter tube; a hub having a distal section and a proximal section, wherein the distal section is joined to the catheter tube and the proximal section defines a housing; a needle extending through the hub and the catheter tube and defining an axial direction, wherein the needle has opposite proximal and distal ends, the distal end forming a needle tip; a needle hub attached to the proximal end of the needle; a needle guard slidably arranged on the needle, wherein the needle guard is movably retained in the housing of the hub when the needle extends through the hub and the catheter tube, and wherein the needle guard is removable from the hub once the needle tip is received in the needle guard upon withdrawal of the needle from the catheter tube; wherein the hub is made of two parts i.e. first part and second part wherein each of the parts having a distal end section and a proximal end section. The second part defines the housing to receive a needle guard which is movably arranged on the needle shaft.

A chamber may be formed by an indentation in the housing for accommodating the first and second arm of the needle guard such that none of the arms deflected by the needle contacts an inner surface of the chamber. Through such indentation the overall outer dimensions of the housing and the catheter hub can be kept small, where it is still provided that the first and second arm of the needle guard does not contact the inner wall surface of the chamber. The space between the arms of the needle guard and the walls of the chamber formed by the indentation of the walls of the catheter hub ensures that there is a significantly reduced drag force at play during the retraction of the needle hub from the catheter. This, in turn, results in the decrease in the discomfort of the patient.

The inner surface of the chamber may be parallel to the axial direction and defined only by one of the first or second part. Preferably the inner surface of the chamber is defined by either the distal end section of the second part or the proximal end section of the second part. More preferably the inner surface of the chamber is defined by the proximal end section of the second part.

Further, the first and second parts of the catheter hub may be joined by complementary end portions, which preferably as such extend at an angle with regard to the axial direction. This ensures that both parts are aligned concentrically towards each other. Thereby, the assembly of such a catheter hub can be made easier.

These end portions may be stepped, which enlarges their contact area for a better mutual interconnection. The end portions may also be slanted for a better mutual interconnection.

In a further embodiment, the first part of the catheter hub comprises an annular ring. The second part comprises a counterpart groove in the inner surface of said second part. The annular ring and the counterpart groove ensure that the first part and the second part are fit together. It is also possible to join the two parts to one another, for example, via a quick-connect fitting, a threaded connection, by interference, a snap-fit, a press-fit, screwed on or a combination thereof, or by any method of attachment known in the art.

In a further embodiment, the first part of the catheter hub comprises of a groove in the outer wall of the distal part which has a counterpart annular ring in the inner surface of the second part. The annular ring and the counterpart groove ensure that the first part and the second part fit together.

In a further embodiment, the first part/the second part of the catheter hub may have an annular ring which is discontinuous with periodic projections and the other part i.e. the second part/the first part may have complementary grooves to accommodate the aforesaid periodic projections.

The hub is also connected to ports adapted to receive infusion fluid through a fluid passage. The ports are connected to the hub though the fluid passage by a passageway. The hub is also provided with wings which in use may be adhesively taped to the skin of the patient at the venipuncture site to maintain the apparatus stationery or steady during the infusion.

According to a preferred embodiment, the retaining protrusion is part-circular, in particular semi-circular shape. More specifically, the retaining protrusion may have generally parallel proximal and distal faces and/or a convex, in particular part-cylindrical, peripheral surface.

According to another embodiment, the first retaining protrusion is arranged in the region of a distal end of the first arm.

According to yet another embodiment, a second disk-like retaining protrusion is arranged on the second arm and adapted to engage with the retaining depression as long as the first arm is in its deflected state.

According to yet another embodiment, the second arm can be deflected along its entire length radially inwards when the needle tip is received between the arms, to thereby allow the second retaining protrusion to disengage from the retaining depression.

According to yet another embodiment, the second retaining protrusion is arranged in the region of a distal end of the second arm. In particular, the second retaining protrusion may be arranged opposite from the first retaining protrusion.

According to yet another embodiment, the retaining depression is an at least part-annular depression, preferably an annular depression.

In a further embodiment of the needle guard, a tension element surrounds the first and second arms of the needle guard. In the deflected state of the first arm, the tension element is expanded against a restoring force of the tension element. Once the needle shaft no longer supports the distal wall of the first arm, the tension element aids the repositioning of the first arm back into axial alignment with the axial direction. This repositioning is necessary so that the distal wall can block the needle tip from axially sliding out of the needle guard. In addition, the tension element helps to enclose a space between the first and second arms and thus helps to prevent the needle shaft and the needle tip from projecting sideways out of the needle guard. In other words, the tension element adds to the protective effect of the needle guard.

Thus, the restoring force is created by at least one of an elastic property of the first arm and an additional tension element. For example, the needle guard may comprise a tension element at least partly surrounding the arms in a region proximal of the first retaining protrusion or—instead of surrounding the two arms—biasing the two arms by a linear biasing action. Alternatively or additionally, the first and second arms can be made of a resilient material having elastic properties.

According to yet another embodiment, the said tension element is integrally mounted to mounting features provided on each of the arms. The mounting features may comprise one or more mounting projections and/or mounting recesses.

According to yet another embodiment, the tension element is integrally mounted onto the arms being adapted to form a partial sidewall such that together with the arms it defines a chamber surrounding the needle in which the needle tip is held after complete withdrawal of the needle from the medical apparatus once the said arms snaps together protecting the needle tip.

According to yet another embodiment, the tension element is placed at a certain gap from the protrusions on the first and second arm. The gap ensures that the restoring force of the tension element snaps both the arms back in position after the needle passes through the needle guard. The gap also further functions at reducing drag while retracting the needle due to which the discomfort experienced by the patient whose venipuncture has occurred reduces significantly.

Further features of the invention provides for the said integrated resilient member or tension element to comprise a ring like integrated form/structure partially or fully surrounding the arms, and/or clamp, bracket, "C" clip or the like surrounding the jaws only in part.

Additional alternative embodiments of the invention include various combinations of the above variations of the needle guard. In other words, the needle guard may be inside and/or outside the second part of the catheter hub. As an example, the needle guard may be partially inside and partially outside the catheter hub, or the needle guard can be wholly outside the catheter hub.

In a further embodiment, the internal walls of the second part of the catheter hub close in to form a neck at the distal portion of the second part. The neck forms the demarcating portion between the first part of the catheter hub and the first part of the catheter hub. The neck ensures that the needle guard does not move in an axial direction, escapes through the opening created by the neck arms and gets in contact with the first portion of the hub. Therefore, the needle guard is confined to the needle guard chamber.

According to yet another embodiment, the needle comprises an engagement mechanism provided at a distance from the needle tip for engaging with the needle guard and preventing the needle guard from sliding off the needle. Preferably, the engagement mechanism is formed by enlargement of the radial dimension of the needle in at least one direction as compared with a principal profile of the needle. The engagement mechanism can be found by a local crimp, a shoulder, a bulge formed as an annular widening etc.

In a further embodiment of the needle guard, a recess is provided in the proximal region of the first arm of the needle guard. This recess increases the deflectability of the first arm in the region it is provided and thereby reduces the restoring force acting on the distal wall while this is being supported by the needle shaft. This allows the needle shaft to be moved more easily relative to the distal wall, as the frictional force acting on the needle shaft is reduced. In an alternative embodiment, the said recess can be provided in both first and second arms.

In a further embodiment of the needle guard, a groove is provided in a side of the distal wall, with the groove extending substantially in the axial direction. The groove acts as a guide groove for the needle shaft and aids the axial movement of the needle shaft relative to the needle guard. Moreover, the needle shaft is prevented from sliding sideways off the distal wall. Such a sideways movement would significantly increase the force required to move the needle shaft relative to the needle guard, which would prevent a correct functioning of the needle guard. In an alternative embodiment, such a groove is provided in both first and second arms.

The needle guard may also include a stopper which is arranged in the needle guard. The stopper is made of a second material different from the first material and has a through-bore with a profile which is adapted to the principal outer profile of the needle shaft. In the case of e.g. circular cross-sections, a diameter of the through-bore can be slightly larger than a principal outer diameter of the needle. The needle shaft, the through bore of stopper and the bore in the base portion of the needle guard are closely and snuggly arranged or the arrangement is a close fit arrangement. The stopper, may be formed by a washer integrally formed within the base portion.

Preferably, the second material is of greater hardness and/or stiffness than the first material. For example, the first material could be a plastic material and the second material could consist of a metal, a ceramic or a rubber material, or any other type of material which is stiff and not as easily distorted as the first material.

The stopper can be arranged anywhere between the base portion and distal region of the first and second arm. For example, the stopper may be arranged within the base portion. Also formed from a different material, it can be integrated therein. As a preferred alternative, the stopper may be arranged loosely on the needle between the two arms of the needle guard and floating on the needle shaft. In this embodiment, the stopper may be formed by a tube-like element. It can be held by holding mechanisms, like a recess or protuberances in a predetermined section of the needle guard. Because of the movability of the stopper relative to both the needle and base portion, the force that has to be applied for pulling the needle through the needle guard upon withdrawal of the needle is reduced.

The stopper can be a circular disk, a ring, or a washer. However, it need not necessarily be circular and can have any other geometric shape such as a rectangular square or triangular shape.

In order to allow a trouble free movement of the needle relative to the needle guard when the needle is withdrawn from the catheter tube, the stopper is preferably arranged such that its through-bore is in general alignment with the needle passage of the needle guard.

According to an embodiment, the stopper completely surrounds the needle. The length of the stopper, i.e. its dimension seen in the axial direction, may vary. As such, the stopper can, for example, be a disk, a ring, or a tube. According to an alternative embodiment, it is also possible that the stopper only partly surrounds the needle. In this case, the stopper could have the shape of a slotted disk, ring, or tube. Furthermore, it has to be understood that outer profile of the stopper does not have to have a circular outer profile. It is also possible that the outer profile of the stopper is of non-circular form, for example, of oval or polygonal shape.

According to an embodiment, the stopper is arranged in the base portion. For example, the stopper can be arranged in a cavity or cut out provided in the base portion. Alternatively, the stopper can be arranged between the first and second arms.

According to yet another embodiment, the needle comprises at least one lateral opening covered by the tubular catheter. At least one lateral opening provides communication between a lumen of the needle and an interior of the tubular catheter. In the event of first venipuncture blood entering the lumen of the needle can exit the needle through the lateral opening and thus become visible for the person handling. At least one lateral opening is preferably large enough in order to provide an early blood flashback function within the tubular catheter such that the practitioner can recognize that he has placed the needle correctly within a patient's vein. In case of a correct positioning of the needle, blood pours out of the opening within the needle shaft into the space between the needle shaft and the inner wall of the transparent tubular catheter and is visible to the practitioner. Preferably, at least one lateral opening is positioned close to the needle tip so that the blood does not have to travel the length of the needle to enter the needle hub in order to become visible. Instead, blood entering the lumen of the needle upon venipuncture partly exits the needle again near the needle tip, thereby becoming particularly quickly and, thus, allowing for particularly fast venipuncture confirmation. The lateral opening has a size which does not obstruct the arms of the needle guard.

The invention also provides a fluid administration medical apparatus including a needle guard in accordance with the present invention. The medical apparatus further including a catheter tube, a hub and a needle having a needle shaft, a needle tip and a needle hub, wherein the needle shaft has a distal section and a proximal section, with at least the proximal section having a principal outer profile.

The needle also may have an enlargement provided between the distal section and the proximal section of the needle shaft. The enlargement has an outer profile one dimension of which is larger than a maximum dimension of the profile of the through bore of the stopper. In a preferred embodiment, the enlargement is made by a crimping of the needle shaft. However, other ways of forming the enlargement are possible, such as applying additional material to the needle shaft, e.g. by soldering, welding or gluing etc.

The inner profile of the needle can either be reduced in the region of the enlargement, for example, if the enlargement is formed by crimping, or it can be substantially constant throughout the length of the needle, for example, if the enlargement is formed by applying additional material to the needle shaft.

Another embodiment is an intravenous catheter apparatus comprising: a housing defining a chamber; a needle received in the chamber; a needle safety device, in particular of the aforementioned kind, slideably arranged on the needle; and an at least part annular relieving depression formed at an inner surface of the housing for receiving a locking shoulder or protrusion of the needle safety device.

By receiving the locking shoulder or protrusion of the needle safety device in the at least part annular relieving depression, the needle safety device is safely held in the chamber of the housing as long as a second jaw of the needle safety device is deflected radially outwards with respect to a first jaw of the needle safety device, i.e. as long as the jaws are spread apart, as is the case when the needle extends all the way through the needle safety device.

According to one of the embodiments, the present invention relates to an intravenous catheter assembly comprising: a catheter tube; a catheter hub having a distal section and a proximal section, wherein the distal section is joined to the catheter tube and the proximal section defines a housing; a port provided on the catheter hub forming an opening into the inner space covered by a port cap, a needle extending through the catheter hub and the catheter tube and defining an axial direction, wherein the needle has opposite proximal and distal ends, the distal end forming a needle tip; a needle hub attached to the proximal end of the needle. The hub is also provided with wings which in use may be adhesively taped to the skin of the patient at the venipuncture site to maintain the device stationery during the infusion.

The port in the catheter assembly forms an opening into the inner space which can be covered by a port cap. In one of the embodiments, a first valve is provided adjacent to the port opening that provides selective access through the port. Fluid may be infused and withdrawn from the catheter through the port without the problem of leakage/outflow or risk of blood exposure. Thus, the port forms a first fluid path from the external environment into the inner space of the catheter assembly. The first valve provided in the first flow path further provides the ability to infuse and withdraw liquids through the port. Thus, the valve on or in the port provides a number of benefits when used with blood control-type catheter assemblies.

The catheter assembly is also provided with a second valve in the inner space which selectively seals a proximal end of the inner space of the catheter housing. Placing the second valve in the catheter hub avoids the problems of outflow of fluid for example, when the second valve is in the path of an introducer needle in the inner space of the catheter hub. The second valve is configured with a plug which is also housed in the inner space of the catheter hub.

Accordingly, in some implementations of the invention, the first valve adjacent to the port opening is utilized with a catheter assembly having an internal blood control second valve. The second valve include a blood control septum. The blood control septum is provided to allow selective flow of fluid through the fluid pathway. For example, the blood control septum may include a slit that may be bypassed when an external luer device is coupled to the hub of the catheter assembly and directly engaging the septum. Upon removing the external luer device, the slit is closed to prevent blood from leaking out of the catheter assembly.

A septum activator may also be located within the inner space at a location that is behind the second valve. When a separate luer device is inserted into the proximal end of the catheter hub, the septum activator is advanced forward through the blood control septum of the second valve, activating the blood control septum. The septum activator generally comprises a tubular body that is rigid or semi-rigid. The tubular body further comprises an inner lumen for facilitating flow of a fluid and/or liquid through the septum activator. The distal end of the tubular body can be shaped and sized to compatibly enter within the one or more slits of the blood control septum of the second valve.

The valves provided can be of various types which can be incorporated into the port and the inner space in the catheter housing to provide medical personnel with the ability to infuse and withdraw fluids from the catheter assembly. The valve can be a one-way valve or a two-way valve. A two-way valve is a valve that permits fluid flow in two directions through the valve when the valve is open. Non-limiting examples of a two-way valve include a split septum, a ball valve, and an iris valve or the like. Thus, a two-way valve can permit fluid to be introduced into the catheter assembly (a first way) and to be withdrawn from the catheter assembly (a second way).

In some embodiments, the valve is a one-way valve, which is a valve that only permits substantial fluid flow in a single direction when the valve is open. A non-limiting example of a one-way valve is a check valve.

The valve can be housed inside the port or in the inner space provided in the housing of the catheter assembly. These valve types are not presented as an exhaustive set of valve types, and thus it will be understood that other suitable valves can be utilized in port and the catheter assembly.

In further embodiments of the invention, the first valve can be located on a removable luer access connector that can be connected and disconnected from the port. Alternatively, the first valve can be located on a luer access connector that is fixedly connected to the port. The first valve can be a luer access valve that accommodates the insertion of a luer device, such as those commonly used in the medical industry. Moreover, a body portion of the port can include luer threads or other connecting and/or fastening features that can secure a luer device to the catheter assembly.

In some configurations, the port can be disposed at an angle relative to the longitudinal axis of the catheter in order to modify the direction at which fluids are infused into the inner housing of the catheter assembly. This angle can be between about 10° to about 90°. The angle of the port can be modified to facilitate use, optimize performance, and/or optimize fluid flow within the inner space of the catheter assembly.

The embodiments of the present invention also include the provisions for including a needle guard slidably arranged on the needle, wherein the needle guard is movably retained in the housing of the catheter hub when the needle extends through the catheter hub and the catheter tube, and wherein the needle guard is removable from the catheter hub once the needle tip is received in the needle guard upon withdrawal of the needle from the catheter tube; and wherein the housing defines a chamber at one end thereof ensuring that a first and second arms of the needle guard do not engage or interact with an inner surface of the chamber prior and during venipuncture of a patient. An intravenous catheter assembly of this kind is generally known.

The needle guard serves to prevent a person handling the intravenous catheter apparatus from accidentally coming into contact with the needle tip after placement of the catheter tube in and subsequent removal of the needle from a patient's vein. Thereby, the intravenous catheter assembly helps to avoid unwanted transmission of blood borne diseases.

As well known in the art, the needle may also have a needle feature close to its needle tip, which interacts with a proportional base of the needle guard, e.g. a curving or a bulge or crimp any other change in profile. Thereby, it can be prevented that the needle is retracted out of the needle guard, which is known in the art.

In an embodiment, the catheter hub is made of two parts. The first and second parts being joined together define the housing having an inner space. The first and second part may form the housing, in particular, the distal end section of the first part and the proximal end section of the second part may form the housing, which ensures that no undercut has to be formed in either one of the first and second part.

Further, the first part includes the port defining a first flow path. Alternatively, it is also possible to provide the port on the second part. The first and second parts of the catheter hub may be joined by complementary end portions, which preferably as such extend at an angle with regard to the axial direction. This ensures that both parts are aligned concentrically towards each other. Thereby, the assembly of such a catheter hub can be made easier. These end portions may be stepped, which enlarges their contact area for a better mutual interconnection.

In an embodiment, the inner space of the catheter hub may receive a needle guard which is movably arranged on the needle shaft. The chamber may be formed by an indentation in the housing for accommodating the first and second arm such that none of the arms deflected by the needle contacts an inner surface of the chamber. Through such indentation the overall outer dimensions of the housing and the catheter hub can be kept small, where it is still provided that the first and second arm of the needle guard do not contact the inner wall surface of the chamber.

The inner space of the housing may be parallel to the axial direction and defined by the distal end section of the first part and the proximal end section of the second part of the catheter hub. Alternatively, the inner space of the housing is defined only by one of the first or second part i.e. by either the distal end section of the first part or the proximal end section of the second part. Further alternatively, the inner space of the housing is defined by the proximal end section of the second part. The advantage in this lies in the fact that only one of the two parts forming the catheter hub has to be dimensioned very precisely in order to ensure an inner space with a well-controlled and large enough diameter such that none of the arms of the needle guard when housed in the inner space of the catheter hub contact said inner surface. In this regard, it is advantageous that the inner space of the housing is defined by the first and second part comprising the second fluid path.

According to one of the embodiments of the invention, one of the first or second part of the catheter hub comprises a surface joined with the inner surface of the one of the first or second part, which surface is inclined towards the inside of the housing in a proximal direction of the catheter hub, wherein the surface has a smaller inside diameter at its innermost end than a distance between outermost points of the arms in their deflected state inside the chamber. Preferably, the first part comprises the surface joined with the inner surface of the second part. Preferably, the distal end section of the first part comprises the surface joined with the inner surface of the proximal end section of the second part. Such a surface serves as a stop for the arms of the needle guard when housed in the inner space of the catheter hub in their deflected state such that they cannot be pulled out of the catheter hub in the proximal axial direction as long as the needle deflects them outward in the ready position of the needle guard. On the other hand, the inclination of the surface supports that the arms are directed inwards when the needle guard is pulled out in the retracted position, even if they have been plastically deformed by the needle in their deflected state.

In some embodiments, an antimicrobial coating is applied to one or more surfaces of the intravenous catheter assembly. The antimicrobial coating further includes an antimicrobial agent that is compatible for use in intravenous catheter assembly used for infusion therapy. Non-limiting examples of suitable antimicrobial agents include chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

Accordingly, one of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle; a first valve provided in the inner space in the catheter hub to prevent foreign contamination from entering the catheter hub; a blood control second valve arranged within the inner space of catheter hub to prevent the outflow of fluid during and following removal of the needle wherein the second valve configured with a plug also housed in the inner space of the catheter hub.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub a needle hub attached to the proximal end of the needle having a housing; a needle guard slidably arranged on the needle, wherein the needle guard is movably retained in a needle guard casing and the needle guard casing is movably retained in the housing of the needle hub, when the needle extends through the needle hub, catheter hub and the catheter tube, wherein the needle guard is removable from the needle hub being retained in the needle guard casing once the needle tip is received in the needle guard upon withdrawal of the needle from the catheter tube.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle having a housing; a needle guard slidably arranged on the needle and an upper end of the needle guard is securely retained in the housing of the catheter hub exposing the lower end of the needle guard and wherein in the ready to use position, the entire catheter hub portion with the lower end of the needle guard is securely retained in an inner space of the needle hub.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle having a housing; a needle guard un-slidably arranged on the needle and the needle guard is securely retained in the housing of the needle hub. In this embodiment, there is an advantage that the chances of the failure of the needle guard which is lowered. Further, as the needle guard is arranged in a non-slidable and a non-movable configuration with respect to the transverse direction, there is no sideways movement of the needle tip in protected position.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle having a housing; a needle guard un-slidably arranged on the needle and the needle guard is securely retained in the housing of the needle hub, wherein there is no tension element mounted onto the needle guard. In this embodiment, there is an advantage that the chances of the failure of the needle guard which is lowered. Further, as the needle guard is arranged in a non-slidable and a non-movable configuration with respect to the transverse direction, there is no sideways movement of the needle tip in protected position.

In the aforementioned embodiment wherein, the needle guard is nested within the needle hub, the extension of the first arm with the distal wall is larger as compared to the extension of the first arm with the distal wall wherein the needle guard is not restricted and is placed on the needle shaft. As the degree of extension is higher, the elasticity of the needle guard is retained and the shelf life of the device is extended.

In the aforementioned embodiment wherein, the needle guard is nested within the needle hub, the needle guard may be affixed to the needle hub by methods such as adhesive sealing, ultrasonic welding, heated die, radio frequency sealing, mechanical seal (snap fit), insert molding, laser welding etc. ensuring a leak free joint providing a hermetic seal In additional alternative embodiments of the invention include various combinations of the above variations of the needle guard. In other words, the needle guard may be inside and/or outside the needle hub. As an example, the needle guard may be partially inside and partially outside the needle hub, or the needle guard can be wholly outside the needle hub.

Some embodiments of the present invention further comprise one or more methods for manufacturing an intravenous catheter assembly according to the teachings of the instant invention. For example, in at least one embodiment a method of manufacturing is provided comprising the following steps: 1) providing catheter assembly having a catheter hub which has a proximal end, a distal end and an inner space extending therebetween; 2) placing a side port on a sidewall of the catheter hub and forming a pathway through the sidewall of the catheter hub and in communication with the inner space; 3) disposing a first valve within the inner space and forming a seal between the inner space and the pathway of the side port; and 4) disposing a blood control second valve within the inner space and dividing the inner space into a proximal chamber and a distal chamber. In some instances, a further step is provided for providing a needle guard for securely covering the needle tip once withdrawn from the patient in order to prevent accidental pricking. The needle guard can be housed in the catheter hub or the needle hub or in part within the catheter hub or in part within the needle hub or in part both within the catheter hub or needle hub or within a needle guard casing. Alternatively, a needle guard can be located outside of a catheter hub, such as in a separate hub different from the catheter hub and needle hub. The needle guard of the present disclosure may embody any number or type of prior art guards configured for blocking or covering the needle tip of the needle in protected position.

BRIEF DESCRIPTION OF THE
ACCOMPANYING DRAWINGS

The foregoing and other objects, features, and advantages of the invention will be apparent from the following detailed description taken in conjunction with the accompanying drawings, wherein.

DETAILED DESCRIPTION OF THE INVENTION

Figure 1:
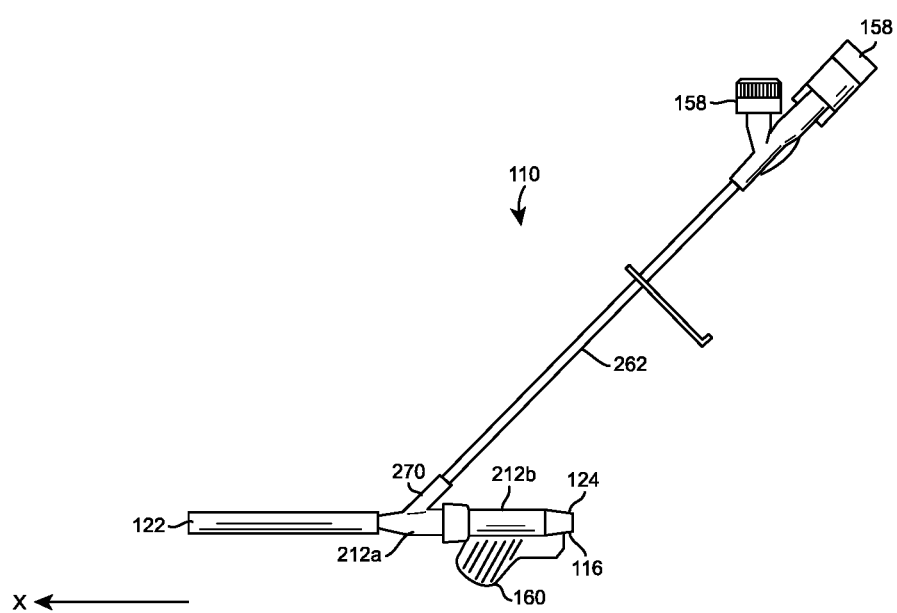
FIG. 1 is a side view of the fluid administration medical apparatus according to the present invention.

Embodiments of the presently disclosed invention will now be described in detail with reference to the drawings wherein like reference numerals designate identical or corresponding elements. In the drawings and in the description, the term "proximal" refers to a region of the apparatus or parts thereof or a location on the apparatus which is closest to, for example, a user using the apparatus. In contrast to this, the term "distal" refers to a region of the apparatus which is farthest from the user, for example, the distal region of a needle will be the region of a needle containing the needle tip which is to be inserted e.g. into a patient's vein.

Embodiments of the presently disclosed invention will now be described in detail with reference to the drawings wherein like reference numerals designate identical or corresponding elements. In the drawings and in the description, the term "proximal", "top", "up" or "upper" refers to a location on the device that is closest to the clinician using the device and farthest from the patient in connection with whom the device is used when the device is used in its normal operation. Conversely, the term "distal", "bottom", "down" or "lower" refers to a location on the device that is farthest from the clinician using the device and closest to the patient in connection with whom the device is used when the device is used in its normal operation. For example, the distal region of a needle will be the region of the needle containing the needle tip which is to be inserted e.g. into a patient's vein.

As used herein, the term "in" or "inwardly" or "inner" refers to a location with respect to the device that, during normal use, is the inside of the device. Conversely, as used herein, the term "out" or "outwardly" or "outer" refers to a location with respect to the device that, during normal use, is toward the outside of the device.

As used herein, the terms first, second, third, etc. are understood to describe different structures so as to distinguish one from another. However, the terms are not structurally limiting unless the context indicates otherwise.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

As used herein "ready position" means the catheter assembly is ready for use, such as to perform a venipuncture or intravenous access. Sometimes the ready position first requires removing a protective cap from the catheter assembly or needle assembly. The protective cap can be included for packaging.

As used herein "protected position" means the catheter assembly in particular the needle hub having a needle is ready for disposal in that the needle tip is safely guarded by a needle guard.

Referring to FIG. 1 a fluid administration medical apparatus 110 having one or more ports 158 in accordance with the present invention is illustrated. The medical apparatus 110 includes a hub 212, a catheter tube 114, a needle 220, handles 160, ports 158 and fluid passage 262. The hub 212 is also connected with ports 158 adapted to receive infusion fluid through a fluid passage 262. The ports 158 are connected to the hub 212 though the fluid passage by a passageway 272.

The handle may be present on one or both sides of the needle hub. The handles 160 may have different shapes that which has been exemplified. The handles have different anti slip devices on their surface like indentation or protrusions on the either of its surfaces.

Figure 2A:
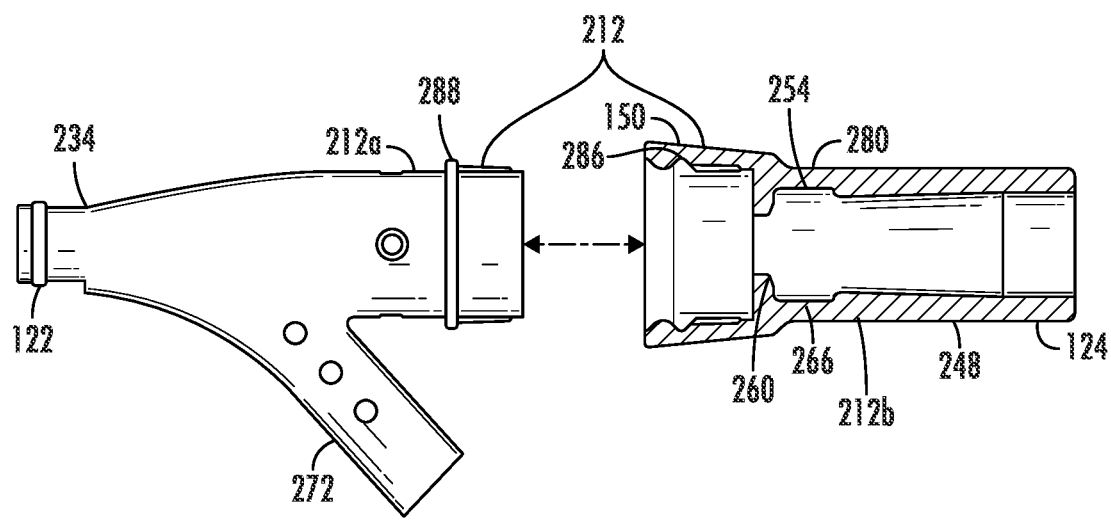
FIG. 2A is a side view of the two parts forming the hub of the fluid administration medical apparatus according to the present invention.
Figure 2B:
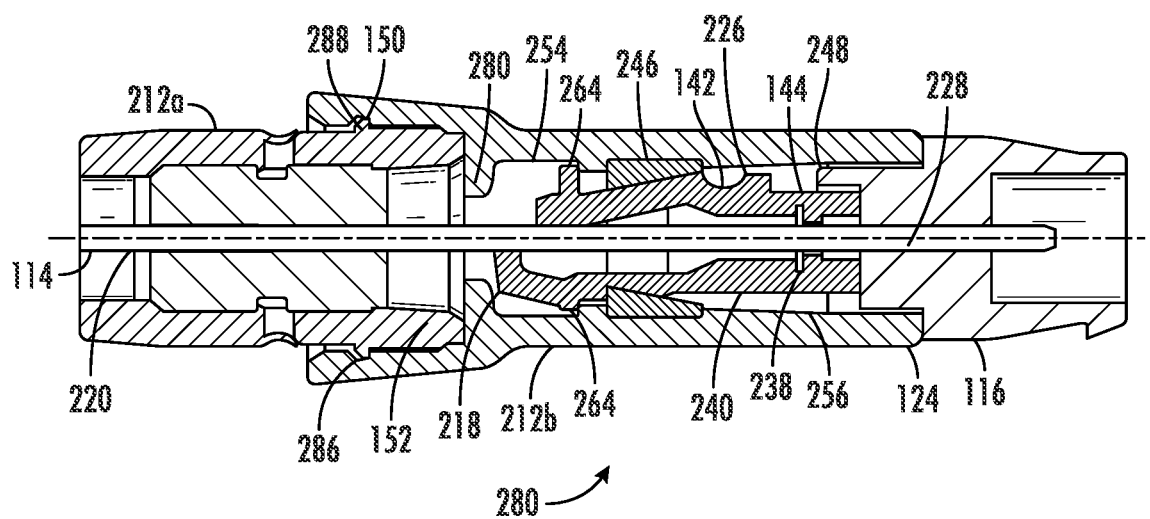
FIG. 2B is a cross-sectional view of hub of the medical apparatus according to the present invention.

As shown in FIGS. 2A and 2B, the hub 212 has a distal end 122 and a proximal end 124; the catheter tube 114 is arranged adjacent to the distal end 122 of the hub 12. The needle 220 has a needle shaft 228, a needle tip 130 at a distal section 234 of the needle shaft 228 and a needle hub 116 attached to a proximal end 136 of the needle shaft 28.

Figure 3:
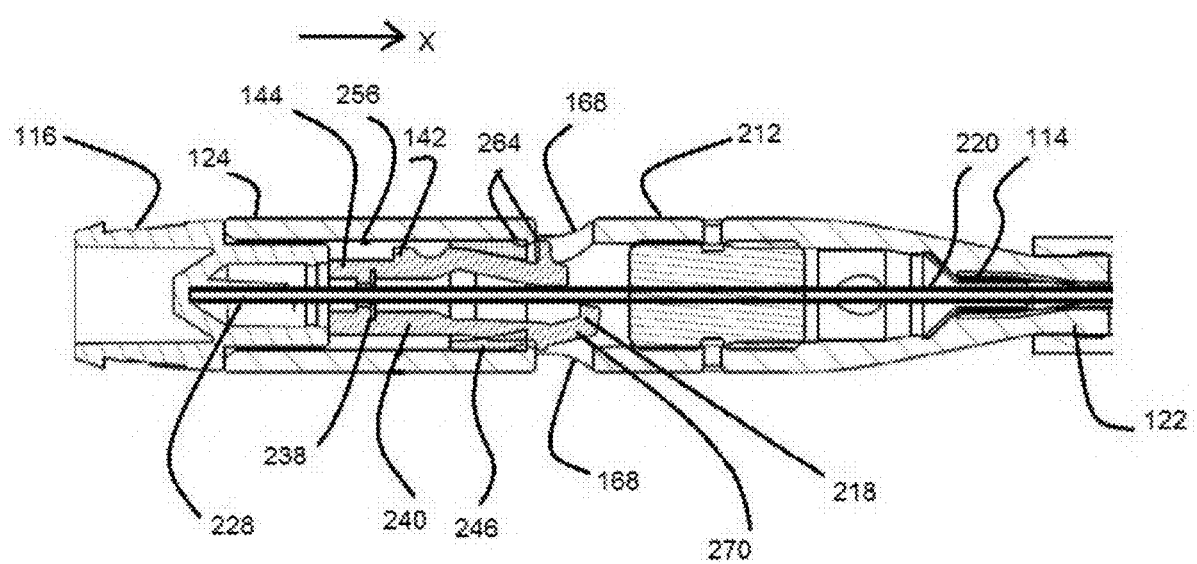
FIG. 3 is cross-sectional view of hub of the medical apparatus according another embodiment of the invention.
Figure 4:
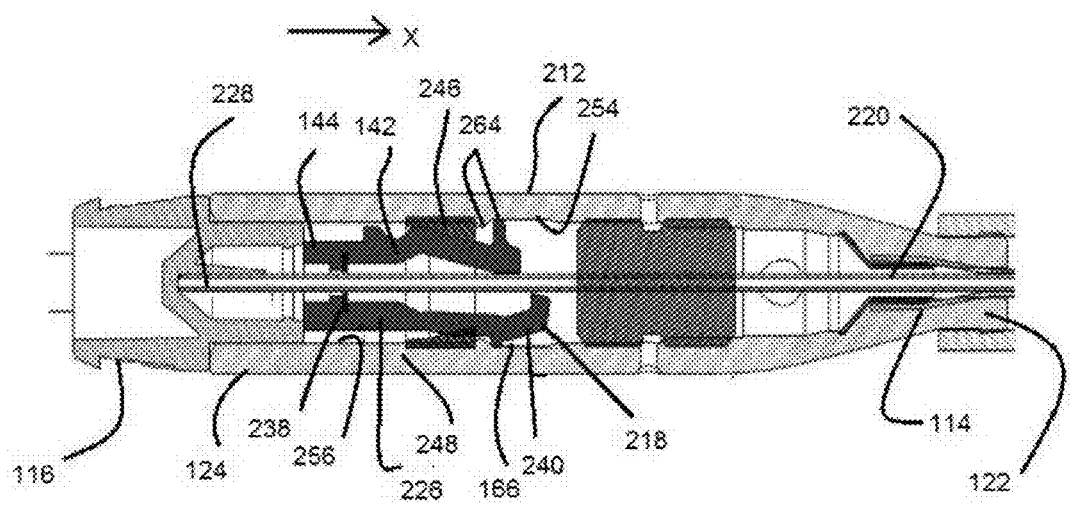
FIG. 4 is cross-sectional view of hub of the medical apparatus according to yet another embodiment of the invention.

Prior to use of the medical apparatus 110, the needle 220 is received in the hub 212 and catheter tube 114, such that the needle shaft 228 extends through the length of the catheter tube 114. A needle guard 226 is movably arranged on the needle shaft 228 and retained in the hub 212 prior to use of the catheter apparatus 110 as shown in FIGS. 2B, 3 and 4. The needle guard 226 has a base portion 144, a first arm 240, a second arm 142 and a distal wall 218. The distal wall 218 is arranged at a distal end of the first arm 240 and extends in a direction transverse to an axial direction X. A tension element 246, for example, a rubber band or the like, surrounds the first and second arms 240, 142. The first and second arms 240, 142 of the needle guard 226 extend generally in the axial direction X from the distal side 160 of the base portion 144, i.e. generally parallel to the needle shaft 228. The ports 158 are used for the administration of fluids to or from a patient through fluid passage 262.

As shown in FIG. 2B, the hub 212 is made of two parts, i.e., first part 212a and second part 212b. Both the parts 212a and 212b have a distal end section 150 and a proximal end section 152. The second part 212b defines a housing 248 to receive a needle guard 226 which is movably arranged on the needle shaft 228. The distal end section of the first part 212a is connected to a catheter tube 114. In particular, as can be seen in FIGS. 2A and 2B, the first and second parts 212a and 212b are joined by complementary stepped end portions 174, 176. Moreover, the first part 212a comprises a surface which is inclined towards the inside of the housing 248 in a proximal direction of the hub 212.

The distal end section 150 of the second part 212b is configured to be assembled with the proximal end section of the first part 212a in various ways in a fluid tight manner. The first part 212a comprises an annular ring 288 in the outer walls of the proximal end section which fits into a counterpart groove 286 in the inner walls of the distal end section of the second part 212b. The annular ring and the counterpart groove ensure that the first part 212a and the second part 212b fit together.

It is also possible to join the two parts 212a, 212b to one another, for example, via a quick-connect fitting, a threaded connection, by interference, a snap-fit, a press-fit or a combination thereof, or by any method of attachment known in the art. The two parts may also be affixed to each other by methods such as adhesive sealing, ultrasonic welding, heated die, radio frequency sealing, mechanical seal (snap fit), insert molding, laser welding etc. ensuring a leak free joint providing a hermetic seal.

As illustrated in FIG. 2B, the housing 248 of the second part 212b of the hub 212 that houses the needle guard 226 is configured such that it defines a chamber 254 at one end of the second part 212b. The chamber 254 is configured to provide room/space for the needle guard 226 in its ready position. In this embodiment, the chamber 254 is arranged in the distal end section 150 of the second part 212b. The chamber 254 is formed by an indentation in the housing 248 for accommodating the first and second arms 240 and 142 such that none of the arms 240 and 142 deflected by the needle 220 contact the inner surface 256 of the chamber 254.

Further, there is a protrusion from the base of the needle hub 116 which lies within the space created by the outer wall of the second arm 142 of the needle guard apparatus and the inner wall of the second part 212b.

In this ready position, the first arm 240 deflects outward of the needle guard 226 such that the distal wall 218 of the first arm 240 is supported on the needle shaft 28. Further, in this ready position, except for the holding mechanisms, the first and second arms 240, 142 do not engage or interact with the inner wall/surface 256 of the chamber 254 prior and during venipuncture of a patient. This reduced non-contact of the first and second arms 240, 142 with the inner wall/surface 256 of the chamber 254 significantly decreases the withdrawal force required and friction caused when a needle 220 is withdrawn through a hub 212 being protected by a needle guard 226 after use.

The chamber 254 terminates at the neck 280 of the second part 212b. The neck 280 ensures that the needle guard apparatus 226 is ensconced in the chamber 254 and does not move in an axial manner towards the needle tip.

Prior to the use of the medical apparatus 110, the needle guard 226 is arranged in the hub near a proximal end 124 of the needle shaft 228. In this situation, the needle 220 extends completely through the needle guard 226, thereby deflecting the first arm 240 of the needle guard 226 outwards, i.e. at an angle to the axial direction X, such that the distal wall 218 of the first arm 240 is supported on the needle shaft 228. Following the insertion of the catheter tube 114 into a patient, the needle 220 is withdrawn from the catheter tube 114 and the needle shaft 228 moves through the needle guard 226 while the needle guard 228 is retained in the hub 112. Once the needle tip 130 passes the transverse distal wall 218 of the needle guard 226, i.e. such that the needle shaft 228 no longer supports the distal wall 218, a restoring force ensures that the first arm 240 of the needle guard 226 is moved back into alignment with the axial direction X of the needle guard 226, so that the needle tip 130 is blocked by the distal wall 218 of the needle guard 226, i.e., the needle tip 130 is prevented from axially projecting out of the needle guard 226.

In one of the preferred embodiments, upon withdrawal of the needle 220 from the catheter tube 114 and hub 212 the needle shaft 228 moves relative to the needle guard 226 until the needle tip 130 is received in the needle guard 226. Once the needle tip 130 is received in the needle guard 226 the enlargement 132 of the needle shaft 228 engages with the base portion 144 of the needle guard 226 via a stopper 238 such that the needle guard 226 can be pulled out of the hub 212 together with the needle 220. An axial movement of the needle 220 relative to the needle guard 226 is now limited, as the distal wall 218 blocks the needle tip 130 and the engagement between the enlargement 132 and the base portion 144 via the stopper 238 prevents the needle tip 130 from being removed via the base portion 144, i.e. the needle tip 130 is safely surrounded by the needle guard 226.

The fact that the stopper 238 is made from a second material which is harder and less easily distorted than the first material of the base portion 144, has the effect that the needle guard 226 is secured more effectively on the needle shaft 228 and can be retained even if excessive external force is applied when pulling on the needle, as the enlargement 132 is prevented from being pulled through the base portion 144 of the needle guard 226 due to the stopper 238.

The stopper 238 is made of a material different to the material of the base portion 144, in particular, a material having a greater hardness and/or stiffness than the material of the base portion 144. Preferably, the stopper 238 is made of metal or ceramic, but it can be made out of any other material which is stiff and is not easily bent.

In one of the preferred embodiments, upon withdrawal of the needle 220 from the catheter tube 114 and hub 212 the needle shaft 228 moves relative to the needle guard 226 until the needle tip 130 is received in the needle guard 26. Once the needle tip 130 is received in the needle guard 226, the attachment mechanism between the first and the second chamber is such that the second part 212a and the needle guard 226 detached from the first part.

The base portion 144 and first and second arms 240, 142 of the needle guard 226 can be made from a plastic material, for example by a moulding process. Hence, it is prevented that the needle guard 226 is removed from the needle tip accidentally. As a result, the needle guard 226 provides a better protection against accidental pricking and thus increased safety for the person handling the medical apparatus.

In order to retain the needle guard 226 in the hub 212 while the needle 220 is being withdrawn from the catheter tube 114, the protrusions 264 provided on both the first arm 240 and the second arm 142 of the needle guard 226 engage with depressions 166 or protrusions 264 or combinations thereof provided on the inner circumferential surface of the hub 212. The protrusions 264 may form an annular ring extending along the entire inner periphery of the hub 212, or they may form one or more ring segments extending along only a respective part of the inner periphery of the hub 212. Similarly, the depressions 166 may form an annular groove extending along the entire inner periphery of the hub 112, or they may form one or more groove segments extending along only a respective part of the inner periphery of the hub 212.

In another embodiment, the needle hub has a projection 280 which juts into the space between the walls of the second part of the needle hub and the needle guard. The projection is semi-circular in nature. The projection 280 ensures that the needle guard does not rotate in the position inside the catheter hub and does not move in a radial direction. The projection 280 is placed in such a manner that there is a gap between the projection and the second arm in the axial direction.

In another embodiment, the projection at the base of the needle hub 284 is fixed with the proximal end of the second part of the catheter hub. This ensures that the needle guard does no undergo axial rotation.

In one embodiment as shown in FIG. 3, the hub 212 may be also formed with a through-hole forming a window or opening 168 which provides sufficient space for a distal radially outer portion 270 of the first arm 240 and second arm 142 in the region of the distal wall 218 such that in the ready position shown in FIG. 3 the distal radially outer portion may deflect to such an extent that it protrudes into the window 168 formed by the through-hole. The window 168 additionally provides a holding function in order to prevent an axial movement of the needle guard 226.

Once the needle 220 has been withdrawn such that the needle tip 130 has passed the distal wall 218 and is received between the first 240 and second 142 arms, the needle shaft 228 no longer supports the distal wall 218. This causes the first arm 240 to reposition itself in axial alignment with the needle 220 due to the restoring force acting on the first arm 240 in its deflected state. The realignment of the first arm 240 is aided through the inherent biasing force of the first arm 240 and additionally through the use of the tension element 246. The realignment of the first arm 240 causes the protrusions 264 to disengage from the depressions 166 or protrusions 264 in the hub 212 allowing the needle guard 226 covering the needle tip 130 to be removed from the hub 212 together with the needle 220, with the guarded needle tip 130 being arranged in a space which is bounded by the base portion 144, the first and second arms 240, 142, the distal wall 218 and the tension element 246.

The catheter apparatus 110 is particularly inexpensive to manufacture if the base portion 44, the first and second arms 240, 142 are integrally made from a first material. The first material may, for example, be a plastic material. Thus the base portion 144, the first and second arms 240, 142 could be manufactured by injection molding.

Alternatively, the base portion 144, one of the first and second arms 240, 142 could be integrally made from a first material, e.g. a plastic material, and the other one of the first and second arms 240, 142 could be made from a second material different from said first material. For example, said other one of the first and second arms 240, 142 could include a strip of material having spring-like properties, e.g. a strip of sheet metal.

The strip of sheet metal may be attached to the base portion at a proximal end face thereof. In this context, the term distal designates the side of a structural member facing in the direction in which the needle tip points when the needle extends through the needle safety device, whereas the term proximal designates the opposite side.

The strip of sheet metal may have a generally L-shaped form, wherein the long leg of the L-shape extends generally in the axial direction, i.e. generally parallel to the first jaw, whereas the short leg of the L-shape extends generally perpendicularly to the axial direction. The short leg of the L-shape is used to attach the strip of sheet metal to the base portion. The strip of sheet metal may be attached to the base portion by means of a heat sealing connection, by a glued connection or by a welded connection.

According to a second embodiment, the second jaw comprises first and second sections that can be moved relative to each other. The first section may be formed integrally with the base portion, whereas the second section may be connected to the first section by means of a hinge. The second section hence forms the deflectable portion of the second jaw.

The first and second sections of the second jaw may be formed from two separate parts, in which case at least one pin may be formed on one of the sections and pivoted in the respective other one of the two sections.

Alternatively, the first and second sections may be formed from one piece, in which case the hinge could be a film hinge.

Figures 5A, 5B, 5C:
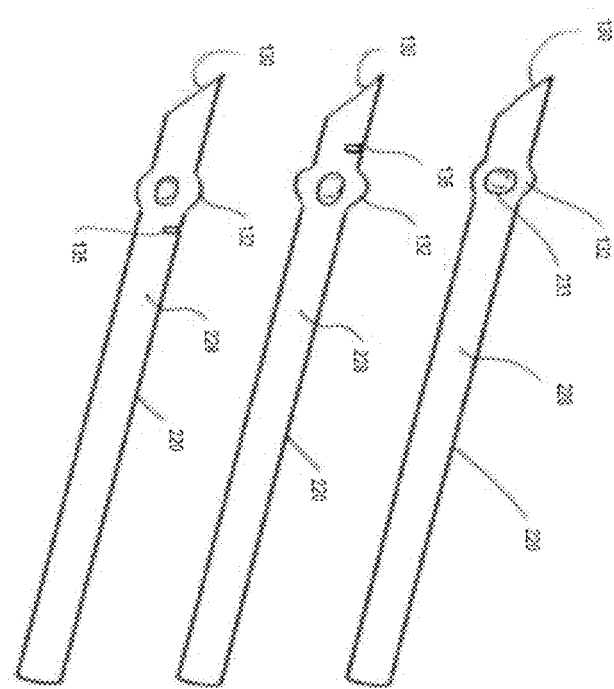
FIG. 5A-5C are different embodiment of needles.

FIG. 5A shows an embodiment of a needle 220 having a needle shaft 228, a needle tip 130 and an enlargement 132. The enlargement 132 of the needle 220 is provided between the distal section 234 and the proximal section 136 of the needle shaft 228. The enlargement 132 has a maximum dimension in a direction transverse to the needle shaft 228, which is greater than the outer diameter of the distal and proximal sections 234, 236. The enlargement 132 can be made, for example, by crimping the needle shaft 228.

The crimp is made by a local depression 233 such that lateral protrusions/enlargement 132 result from the crimping process. The crimping process is controlled such that the internal cross-sectional area of the needle is not reduced substantially such that the through bore or the internal profile of the needle is not affected.

FIG. 5B shows the needle according to FIG. 5A, however having an opening 135 arranged slightly distally from the enlargement 132, such that it is still arranged within the catheter tube in the ready position. The opening 135 just extends over about 0.5 mm in axial direction and provides a through hole through the needle wall. Thereby, an early blood flashback within the transparent catheter tube 114 can be achieved when the needle is position into the patient's vein. Based on this blood flashback, the practitioner can see right after puncturing the patient whether the needle has been positioned correctly due to a small amount of patient's blood flooding the space between the needle shaft 228 and the transparent catheter tube 114.

FIG. 5C shows the needle according to FIG. 5B, however with the opening 135 arranged proximally from the enlargement 132. The opening 135 is dimensioned such that it does not affect the functioning of the needle guard 226. The size of the opening 135 is such that it does not obstruct the arms of the needle guard 226. The arrangement and/or position of the enlargement 132 and opening 135 can be interchanged. The shape of the opening 135 may vary and include shapes such as circular, square, rectangular, curve, oval, semicircular or the like etc.

Figure 6A:
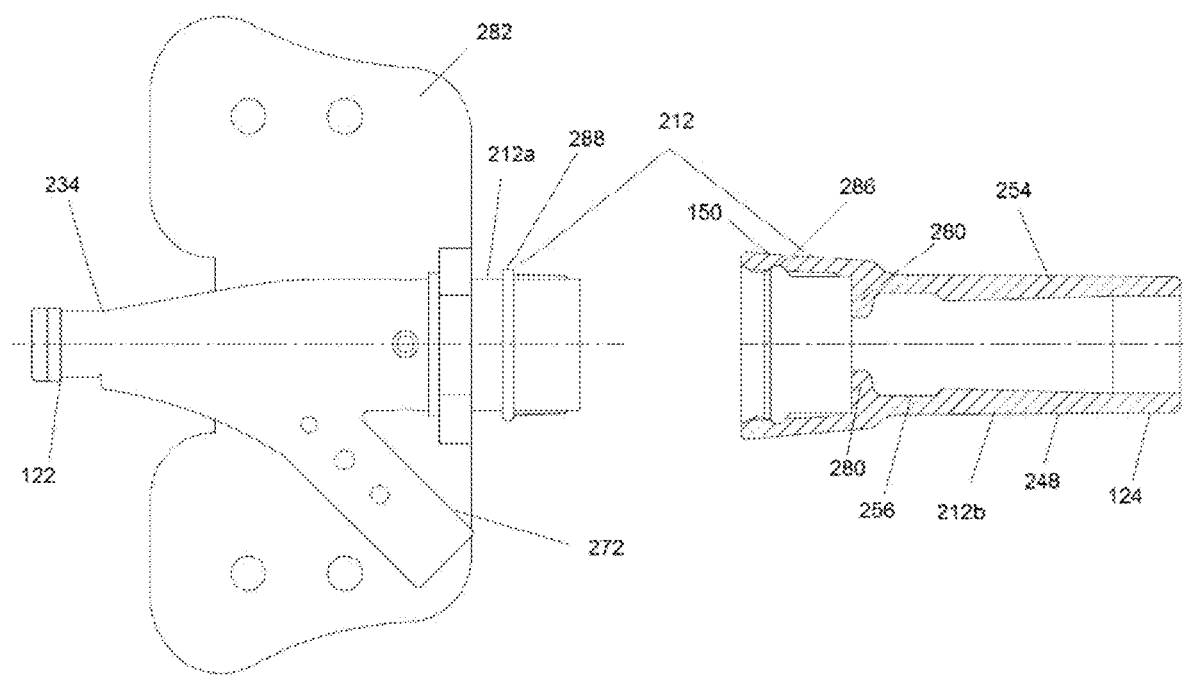
FIG. 6A-6B are different embodiments of the fluid administration medical apparatus according to the present invention.
Figure 6B:
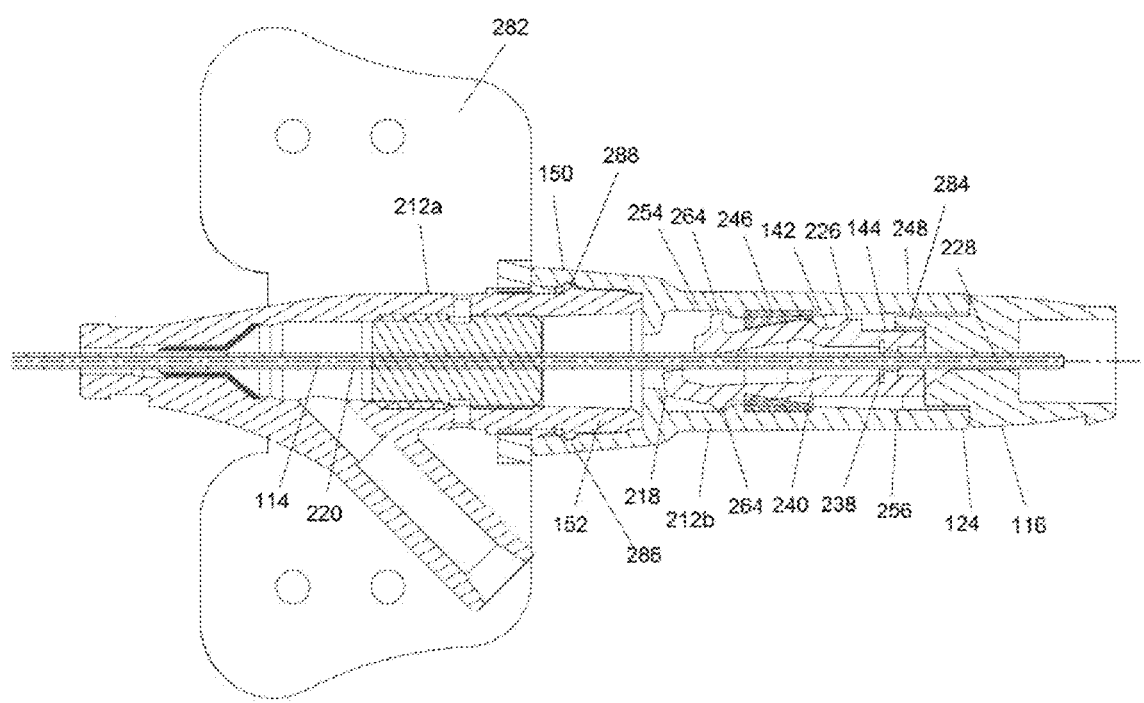

FIGS. 6A and 6B shows another embodiment of the catheter apparatus 110, wherein wings 282 have been incorporated in the second part of the hub 212a. The wings facilitate the affixing of the catheter onto the skin of the patient at the site of venipuncture. The wings may be affixed onto the second part 212a via many various means a quick-connect fitting, a threaded connection, by interference, a snap-fit, a press-fit or a combination thereof, or by any method of attachment known in the art The construction and shape of the improved medical apparatus 110 of the present disclosure provides a simple configuration. The simple design of medical apparatus is advantageous in a clinical setting because it smoothen the whole catheterization process thereby reducing injury or discomfort to patient. In addition, such design greatly reduces manufacturing costs and is efficient, effective and simple in its construction and use.

Figure 7:
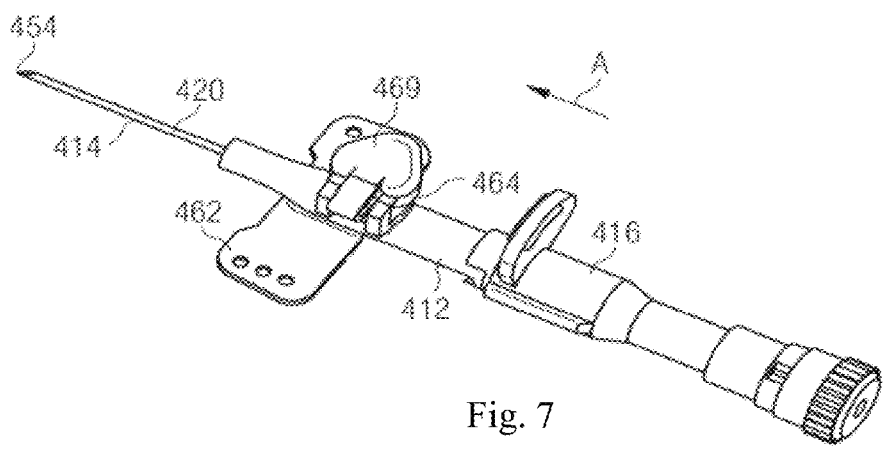
FIG. 7 illustrates an intravenous catheter assembly according to one of the embodiments of the present invention.

Referring to FIG. 7 an intravenous catheter assembly 410 in accordance with one of the embodiments of the invention is illustrated. The intravenous catheter assembly 410 generally comprises various features and elements to enable intravenous infusion of a fluid or medicament into a patient. In some instances, intravenous catheter assembly 410 further comprises feature to enable removal of a fluid from a patient, such as blood. The intravenous catheter assembly 410 includes a catheter hub 412 having a first fluid path 411a and a second fluid path 411b, a catheter tube 414 and a needle 420 attached to a needle hub 416. The catheter hub 412 has a distal end 422 and a proximal end 424, wherein the catheter tube 414 is arranged adjacent to the distal end 422 of the catheter hub 412 with a slip ring 461. The catheter tube 414 generally includes a biocompatible material that is made of a flexible or a semi-flexible polymer. The catheter tube 414 and the catheter assembly 410 are integrally coupled such that an inner space defining a housing 448 of the catheter hub 412 extends into the catheter tube 414. The catheter hub 412 is also provided with wings 462 which in use may be adhesively taped to the skin of the patient at the venipuncture site to maintain the catheter assembly/device 410 stationery during the infusion.

Figures 8A, 8B, 8C:
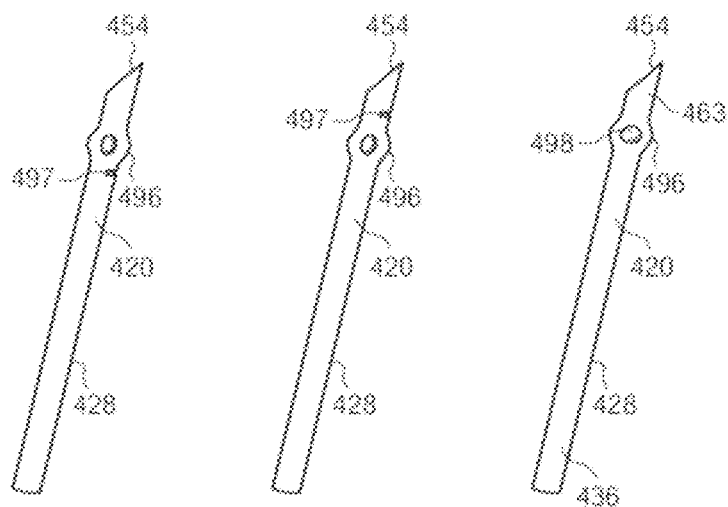
FIGS. 8A-8C are different embodiment of the needles according to the present invention.

Referring now to FIGS. 8A to 8C, the needle 420 has a needle shaft 428, a needle tip 454 at a distal section 463 of the needle shaft 428 and a needle hub 416 attached to a proximal section 436 of the needle shaft 428. An enlargement 496 of the needle 420 is provided between the distal section 463 and the proximal section 436 of the needle shaft 428. The enlargement 496 has a maximum dimension in a direction transverse to the needle shaft 428, which is greater than the outer diameter of the distal 463 or proximal section 436. The enlargement 496 can be made, for example, by crimping the needle shaft 428. The crimp is made by a local depression 498 such that lateral protrusions/enlargement 496 result from the crimping process. The crimping process is controlled such that the internal cross-sectional area of the needle 420 is not reduced substantially such that the through bore or the internal profile of the needle 420 is not affected. Prior to use of the catheter assembly 410, the needle 420 is received in the catheter hub 412 and catheter tube 414, such that the needle shaft 428 extends through the length of the catheter tube 414 and the needle tip 454 is exposed out of the catheter tip. The needle 420 is capable of piercing the skin to provide access to the vasculature or subcutaneous tissues of the patient. Once access is obtained, tip of catheter 414 is inserted through the newly formed opening and into the desired location within the patient. The needle 420 is then withdrawn from the catheter assembly 410, and catheter 414 is left disposed within the patient.

The needle 420 comprises at least one opening 497 covered by the tubular catheter 414. The opening 497 provides communication between a lumen of the needle 420 and an interior of the tubular catheter 414. In the event of first venipuncture blood entering the lumen of the needle 420 can exit the needle 420 through the opening 497 and thus become visible for the person handling. The opening 497 is preferably large enough in order to provide an early blood flashback function within the tubular catheter 414 such that the practitioner can recognize that he has placed the needle 420 correctly within a patient's vein. In case of a correct positioning of the needle 420, blood pours out of the opening 497 within the needle shaft 428 into the space between the needle shaft 428 and the inner wall of the transparent tubular catheter 414 and is visible to the practitioner. Preferably, the opening 497 is positioned close to the needle tip 454 so that the blood does not have to travel the length of the needle 420 to enter the needle hub 416 in order to become visible. Instead, blood entering the lumen of the needle 420 upon venipuncture partly exits the needle 420 near the needle tip 454, thereby becoming particularly quickly and, thus, allowing for particularly fast venipuncture confirmation. The opening 497 has a miniscule size which serves the purpose of early flashback detection and which does not obstruct the arms of the needle guard 426.

The opening 497 can be provided before or after the enlargement 496. In further embodiments of the invention, the needle 420 may also be formed with the opening 497 arranged distally or proximally from the enlargement 496. The opening 497 may be formed by a small slit which is cut into the needle shaft 428 and which extends in axial direction A for about a small distance. The opening 497 is just large enough in order to provide an early blood flashback function close to the needle tip 454 within the catheter tube 414 such that the practitioner can recognize that he has placed the needle 420 correctly within a patient's vein. In case of a correct positioning of the needle 420, blood pours out of the opening 497 within the needle shaft 428 into the space between the needle shaft 428 and the inner wall of the transparent catheter tube 414 and is visible to the practitioner.

Figure 9:
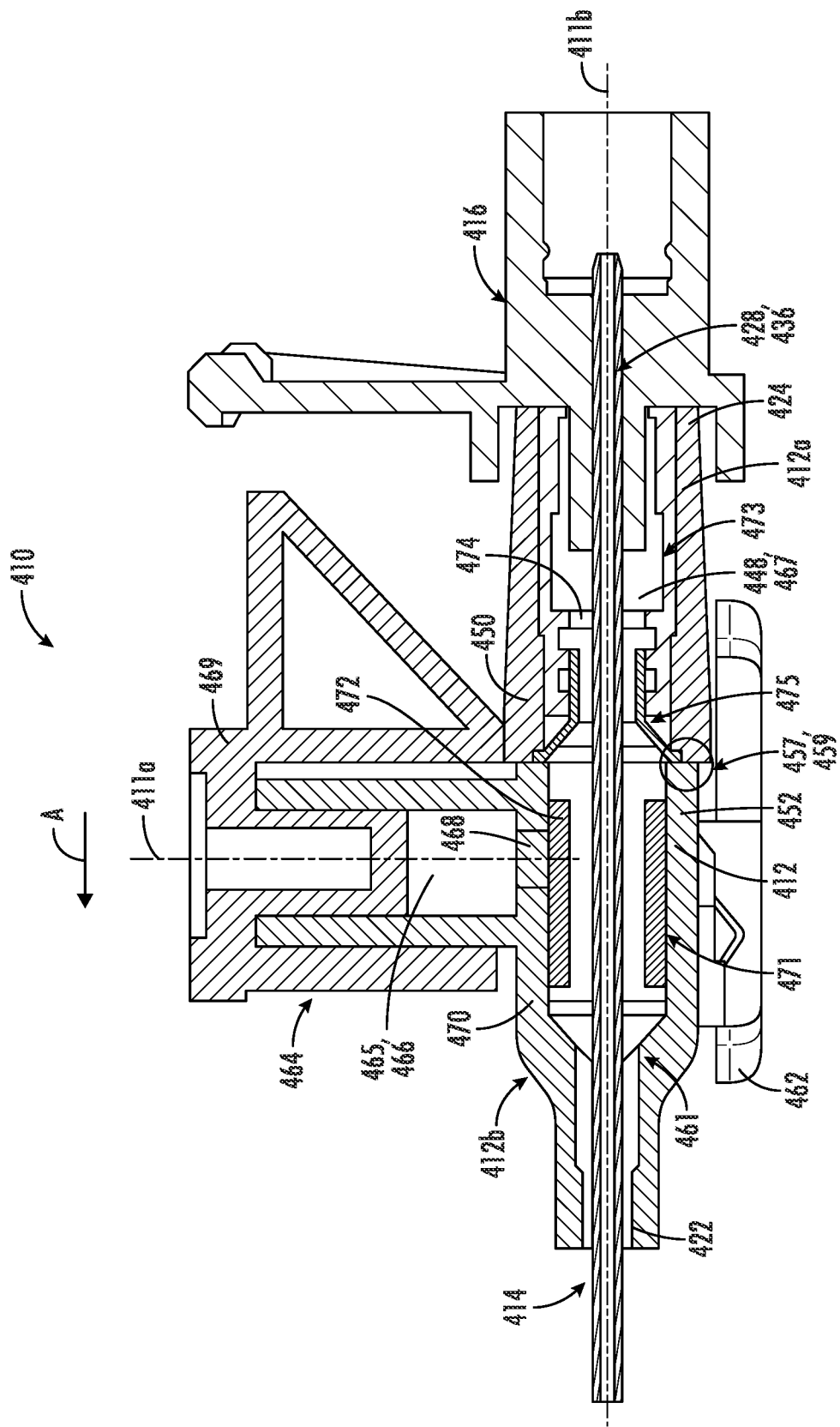
FIG. 9 is a cross-sectional side view of the two parts forming a catheter hub of the intravenous catheter assembly according to one of the embodiments of the present invention.

Referring now to FIG. 9, the catheter hub 412 is made of two parts, i.e. a first part 412a and a second part 412b. The first part 412a has a distal end section 450 and the second part 412b has a proximal end section 452. The distal end 422 of the second part 412b is connected to a catheter tube 414. The distal end section 450 of the first part 412a is configured to be assembled with the proximal end section 452 of the second part 412b in various ways in a fluid tight manner, such as by adhesive sealing, ultrasonic welding, heated die, radio frequency sealing, mechanical seal (snap fit), insert molding, laser welding etc., ensuring a leak free joint. It is also possible to join the two parts 412a, 412b to one another, for example, using threads, interference, or snap-fit. In particular, as can be seen in FIG. 9, the first and second parts 412a and 412b are joined by complementary stepped end portions/surfaces 457, 459.

A port 464 includes a port body having one or more integrated body portions which extend outwardly in a direction perpendicular to the axial direction A from the sidewall 470 of the catheter hub 412. The port 464 has an opening 465 defining an inlet and a bore 466 extending between the inlet and the opening 468 of the inner space 467 of the catheter hub 412. The port 464 and in particular, the inlet 465 and at least a portion of bore 466 is shaped and sized in conformity with the prescribed International Standards Organization (ISO) standards for a female luer connection. This will allow a male luer slip or male luer lock to be connected to port 464. The port 464 is covered with a port cap 469.

The port 464 can be a side port or a top port. Fluids may be infused and withdrawn from the catheter assembly 410 through the port 420 in a sidewall 470 of the catheter hub 412. The sidewall 470 can be any wall of the catheter hub 412 that extends substantially axially along the catheter tube 414.

In various embodiments, the outer periphery and/or inner periphery of the port 464 body can include one or more luer threads or the like in any number of thread configurations available to provide and interlock between mating devices. The luer threads allow another medical device having a male luer lock to be connected to and interlocked with the port 464. Alternatively, the port 464 body can also have no luer threads to accommodate luer slip and luer lock connections.

A first valve 471 is provided in an inner space 467 adjacent to an inlet opening 468 in the catheter hub 412 to prevent foreign contamination from entering the catheter hub 412 that provides selective access through the port 464. The first valve or the sleeve 471 includes a slit 472. The first valve or the sleeve 471 with the slit 472 forms a fluid barrier until by manual pressure/activation/manipulation the slit 472 gives way to allow fluid flow through the slit through. In normal and no pressured situation, the slit 472 remains closed and thereby providing a fluid-tight seal. Thus, premature or accidental fluid leakage into the medical device is prevented. The first valve 471 generally comprises a flexible tube having an outer diameter that is approximately the same size as an inner diameter of the inner space 467 of the catheter hub 412, whereby the first valve 471 is retained within the inner space 467 by an interference fit or by means of change of dimensions.

In one of the embodiments, the activation or opening of the slit 472 is through fluid pressure i.e. automatic, and does not require manual intervention to open the slit. In order to achieve this, it is understood that the first valve/sleeve 471 is not too rigid resulting in a flow back nor is first valve/sleeve 471 too flexible resulting in "bag" formation and accumulation of fluid in the bag.

Figure 10A:
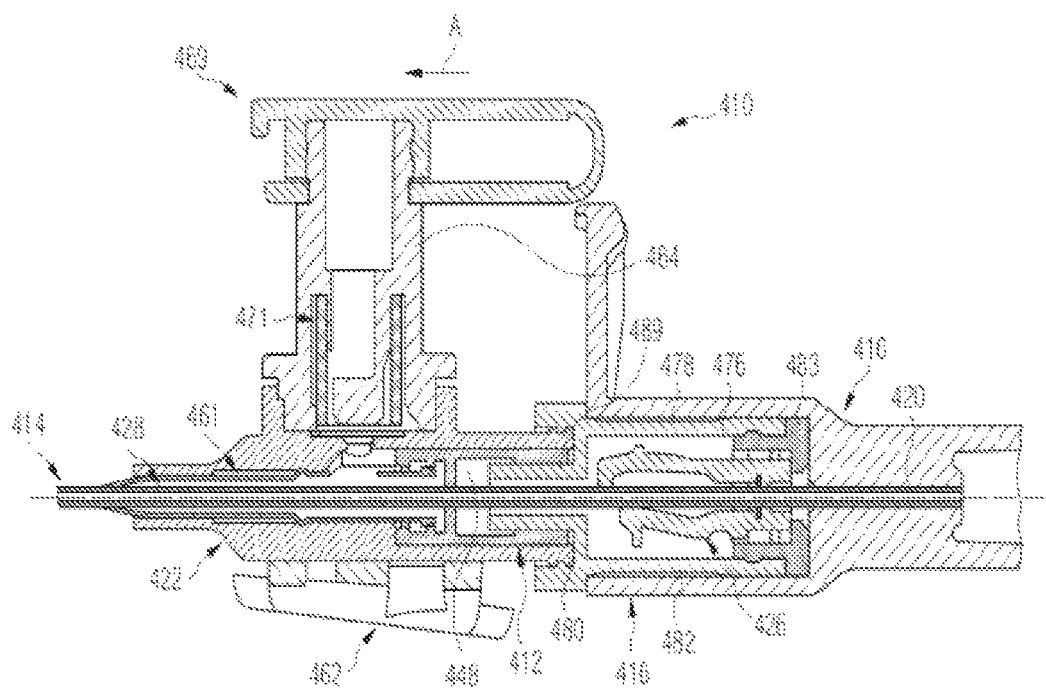
FIG. 10A is a cross-sectional side view of the intravenous catheter assembly showing a side port, a catheter hub, a needle hub and a needle guard casing with a needled guard retained in the needle hub according to one of the embodiments of the present invention.

The first valve 471 can be located on the inlet 465, within the inlet 465, adjacent to the inlet 465, within the bore 466 of the port body 464 or in the inner space 467 adjacent to the inlet opening 468 in the catheter hub 412. As shown in FIG. 10A, the first valve 471 is arranged within the bore 466 of the port body 464.

First valve 471 generally comprises a resilient, flexible material that is easily deformed when fluid is introduced to port 464 via a syringe or other compatible device. Materials such as silicone, silicone rubber, or polyisoprene or the like can be used to form the first valve 471. The first valve 471 can be formed as a single piece of elastomeric material that is formed to having various shapes and features. Alternatively, the first valve 471 can be a two-piece configuration having a flexible inner material, such as silicon or silicone rubber, and a more rigid outer portion, such as an outer ring. The outer ring can be formed of a plastic or metal or other suitable material. The first valve 471 includes at least one slit. Alternatively, first valve 471 can include plurality of slits. In some configurations, at least a portion of the first valve 471 is glued to the port body 464 using one or more adhesives in a fluid tight manner. Additionally, or alternatively, in some configurations, at least a portion of the first valve 471 is held in place between two or more portions of the port body 464 in a fluid tight manner.

The port 464 can be accessed, with a male luer device that is inserted through the slit of the first valve 471. The male luer device can be interlocked with the luer threads if the male luer device includes a luer lock. In this manner, a separate access device can be coupled to the catheter assembly 410 through the port 464 to establish fluid communication therethrough. Additionally, a syringe, needle, or other such device can be inserted through the slit of the first valve 471 to withdraw fluids therethrough. Using the first valve 471, medical personnel can access the inner space 467 of the catheter hub 412 without being exposed to the patient's blood.

A blood control second valve 473 including a blood control septum 474 having at least one slit is arranged within the inner space 467 of catheter hub 412 to prevent the outflow of fluid during and following removal of the needle 420. The second valve 473 is configured with a plug 475 which is also housed in the inner space 467 of the catheter hub 412. The blood control second valve 473 can be elastomeric and be designed to closely conform to the shape of a needle 420 to prevent leaking. The blood control second valve 473 can also seal upon removal of the needle 420 due to axial compression forces on the second valve 473 that induces it to close. The second valve 473 can have an outer diameter that is configured to compatibly seat within a groove or channel or other suitable projections formed on an inner surface of the catheter hub 412. Alternatively, a groove or channel or other suitable projections can be formed on the outer surface of the second valve 473, which interlocks with one or more features on the inner surface of the catheter hub 412.

The second valve 473 is configured with a plug 475 which is also housed in the inner space 467 of the catheter hub 412. The plug 475 is in fluid communication with the second valve 473 and inner space 467 of the catheter hub 412. The inner surface at a distal end of the second valve 473 is provided with at least one projection or groove or vice versa matching with said at least one projection or groove provided in an outer wall/surface of the plug 475 at a proximal end 424 thereof. The plug 475 could be made from a first material, e.g. a rigid plastic material or metal, and the second valve 473 could be made from a second material different from said first material for example, second material of the second valve 473 could be resilient, flexible material that is easily deformed when fluid is introduced to port via a syringe or other compatible device. Materials such as silicone, silicone rubber, or polyisoprene or the like can be used to form the second valve 473. The second valve 473 is spaced from the first valve 471 being positioned within a fluid pathway through the inner space 467 of the hub 412 of the catheter assembly 410.

In some embodiments, the second valve 473 is tube or barrel shaped, while in other configurations, the second valve 473 is substantially cylindrical or disk shaped. The embodiments of the second valve 473 include other geometrical shapes and dimension. The second valve 473 can be elastomeric and include one or more slits through which a septum activator can be inserted. The second valve 473 includes at least one slit. Alternatively, second valve 473 can include plurality of slits. Slit provides a fluid-tight seal, thereby preventing fluid from bypassing septum 474.

The proximal end 424 of the catheter hub 412 further comprises an opening 477 through which a separate secondary device may be inserted to infuse and withdraw fluid and/or liquid, such as a syringe or intravenous fluid line. In some instances, proximal end 424 comprises a set of threads configured to threadedly receive the secondary device in a secure manner. Opening 477 may further comprise a tapered opening to receive secondary device via an interference or friction fit. Proximal end 424 and opening 477 may alternatively comprises various surfaces and other features to enable coupling to a needle hub 416, a diagnostic device, and other suitable infusion therapy equipment.

As discussed above, upon deformation of the first 471 and second valve 473, fluid from the syringe or from the patient is permitted to bypass the deformed valve and flow into inner space 467 of the catheter hub 412. As the fluid pressure decreases, the resilient nature of the valve's 471, 473 material causes valves 471, 473 to restore their original shape, thereby once again blocking the fluid pathway. In some embodiments, valves 471, 473 may be secured within inner space 467 of the catheter hub 412 by any compatible means. For example, valves 471, 473 are secured within inner space 467 via an adhesive. In other embodiments, valves 471, 473 are secured within inner space 467 via an interference fit. Further, in some instances valves 471, 473 are inserted into an annular groove formed on the inner surface of the catheter hub 412. For example, the first valve 471 as shown in FIG. 9. is placed within inner space 467 so as to overlap and form a seal between inner space 467 and the pathway of the port 464. Both the first 471 and second 473 valves comprise a proximal opening, a distal opening, and a pathway extending therebetween. In some instances, proximal opening comprises a reduced diameter. The embodiment shown in FIG. 9 is without a needle guard 426. However, a needle guard 426 can be housed within the housing of catheter hub 412 and/or needle hub 416.

Figure 10B:
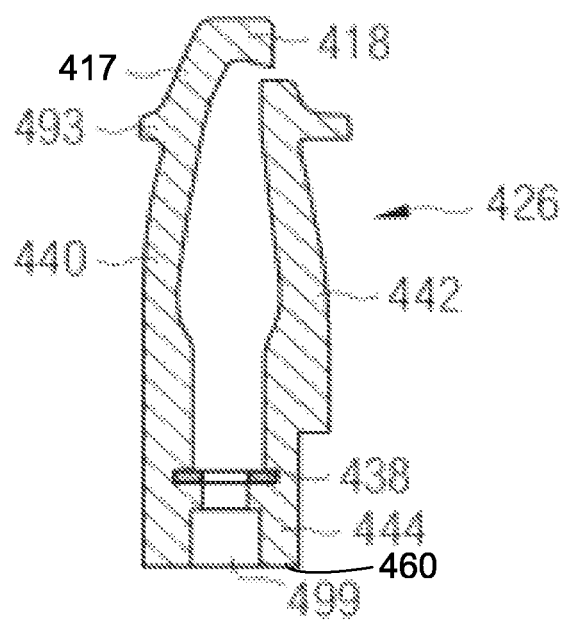
FIG. 10B is a cross-sectional side view of the needle guard of the present invention.
Figure 10C:
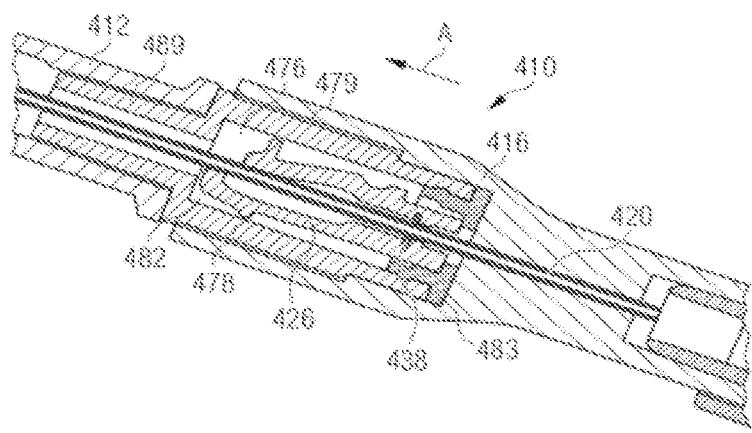
FIG. 10C is a cross-sectional side view of the intravenous catheter assembly showing a catheter hub, a needle hub and a needle guard casing with a needled guard retained in the needle hub according to one of the embodiments of the present invention.
Figure 10D:
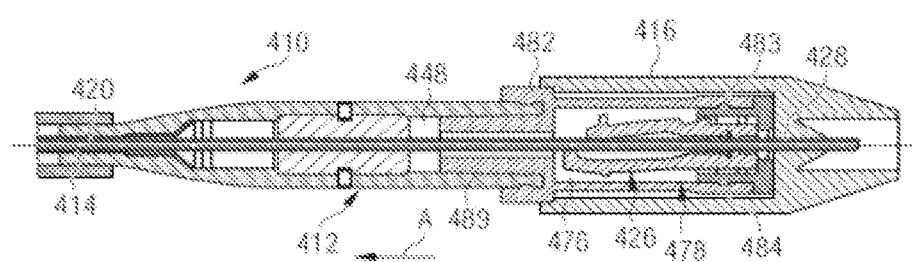
FIG. 10D is a cross-sectional side view of the intravenous catheter assembly showing a catheter hub, a needle hub and a needle guard casing with a needled guard retained in the needle hub according to one of the embodiments of the present invention.
Figure 11A:
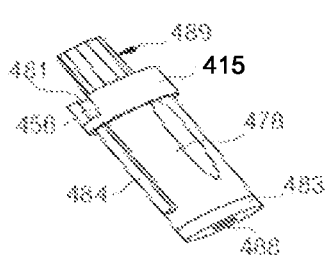
FIG. 11A is a perspective view of the needle guard casing of the present invention.
Figure 11B:
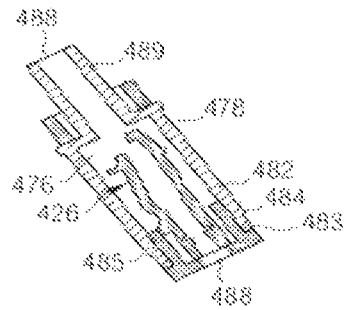
FIG. 11B is a cross-sectional side view of the needle guard casing showing a needle guard housed within according to one of the embodiments of the present invention.
Figure 11C:
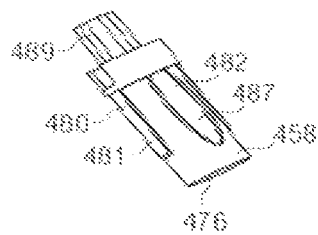
FIG. 11C is a perspective view of the upper part of the needle guard casing of the present invention.
Figure 11D:
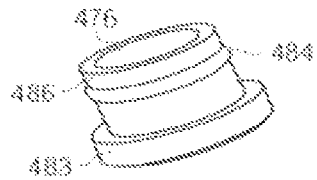
FIG. 11D is a perspective view of the lower part of the needle guard casing of the present invention.
Figure 12A:
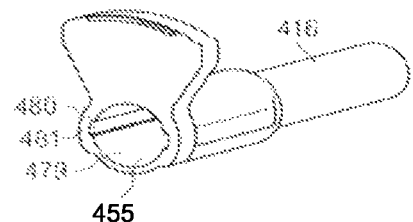
FIGS. 12A & 12B are perspective view of the needle hub of the intravenous catheter assembly according to one of the embodiments of the present invention.
Figure 12B:
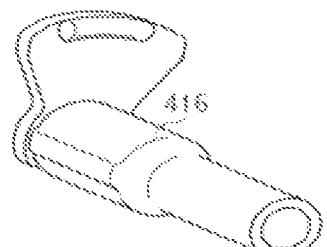

In another embodiment, as shown in FIG. 10A a needle guard 426 as shown in FIG. 10B is movably arranged on the needle shaft 428 and retained in a needle guard casing 478. The needle guard casing 478 can be movably retained in the needle hub 416 prior to use of the catheter assembly 410 as shown in FIGS. 10A, 10C & 10D. The needle hub 416 is provided with inner space 479 defining a housing to movably receive the needle guard casing 478 as shown in FIGS. 12A and 12B. The needle guard casing 478 has a substantially cylindrical shape, which is structurally beneficial to the provision of rotation capabilities.

Referring now to FIGS. 11A to 11D, the needle guard casing 478 comprises an upper part 482 and a lower part 483 together forming a chamber 476 for housing the needle guard 426. The upper part 482 of the needle guard casing 478 is received on the lower part 483. For example, the upper part 482 may be snap-fitted on the lower part 483. The snap-fit may be formed by a protrusion ring 484 and a corresponding groove ring 485 and which can be provided in both upper and lower part alternatively. The protrusion ring 484 may comprise the grooves and the groove ring 485 may comprise at least one projection or vice-versa. The ring of both the projections or groove can be a continuous ring or a spaced apart formation. Other ways and means for a secure engagement are also encompassed.

Both the upper part 482 and lower part 483 of the needle guard casing 478 is provided with a chamber 476 to safely house the needle guard 426. In the upper part 482 the chamber 476 is provided in the bottom portion 487 whereas in the lower part 483 the chamber 476 is provided in the top portion 486. Both the upper part 482 and lower part 483 has a bore 488 to receive the needle 420. The inner diameter of the bore 488 has a close fit ratio with the outer diameter of the needle 420.

A distal end 415 of the upper part 482 is provided with a fitment 489 which is received in the housing 448 of the catheter hub 412 creating a secure connection between the two. The fitment 489 also has a bore 488 which allows the needle 420 to pass there through. The inner diameter of the bore 488 has a close fit ratio with the outer diameter of the needle 420. When the needle guard casing 478 is secured completely within the needle hub 416 the fitment 489 remains exposed to be safely received in the housing 448 of the catheter hub 412. In other embodiments, for a safe and secure connection between the fitment 489 of the upper part 482 and the housing 448 of the catheter hub 412, an outer wall 458 of the catheter hub housing 448 is provided with at least one projection 480 or groove 481 or vice versa matching with said at least one projection 480 or groove 481 may be provided in an inner wall 456 adjoining said fitment 489. Thus, the needle guard casing 478 is safely secured with the catheter hub housing 448 by the means of change in dimensions. Alternative arrangements by way of replacing the change of dimensions within or outside the housing 448 and on the upper part 482 of the needle guard casing 478 can also be employed. For example, the upper part 482 of the needle guard casing 478 can be made without the fitment 489 and be snap-fitted with the catheter hub housing 448. The snap-fit may be formed by a protrusion ring 484 and a corresponding groove ring 485. The protrusion ring 484 may comprise the groove and the groove ring 485 may comprise at least one projection or vice versa. The ring of both the projections or groove can be a continuous ring or a spaced apart formation. Other ways and means for a secure engagement are also encompassed, for example as shown in FIGS. 10A, 10C & 10D. Further, there is a close fit ratio between the inner diameter of the bore 488 provided in the upper 482 and lower part 483 of the needle guard casing 478 and outer diameter of the needle 420.

As shown in FIGS. 12A and 12B, in order to enable the needle guard casing 478 to fit within the housing 479 of the needle hub 416, an inner wall 455 of the needle hub housing 479 is provided with at least one projection 480 and/or groove 481 or vice versa matching with said at least one projection 480 and/or groove 481 is provided in an outer wall 458 of an upper 482 and/or lower 483 part of the needle guard casing 478. Thus, the needle guard casing 478 is safely secured within the needle hub housing 479 by the means of change in dimensions. Alternative arrangements by way of replacing the change of dimensions within the housing 479 and on the upper 482 and lower 483 part of the needle guard casing 478 can also be employed.

Figure 13A:
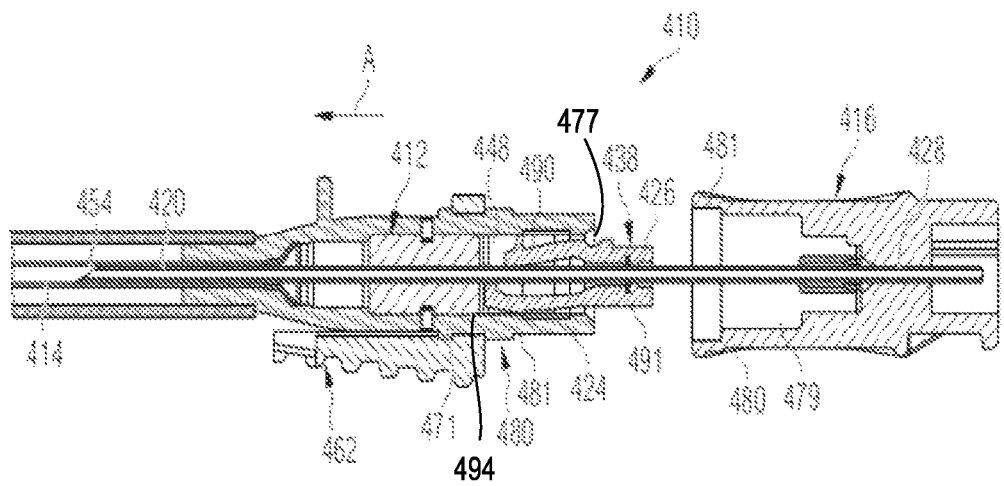
FIGS. 13A & 13B are a cross-sectional side views of the intravenous catheter assembly showing a catheter hub, a needle hub and a needle guard retained in the needle hub and catheter hub according to one of the embodiments of the present invention.
Figure 13B:
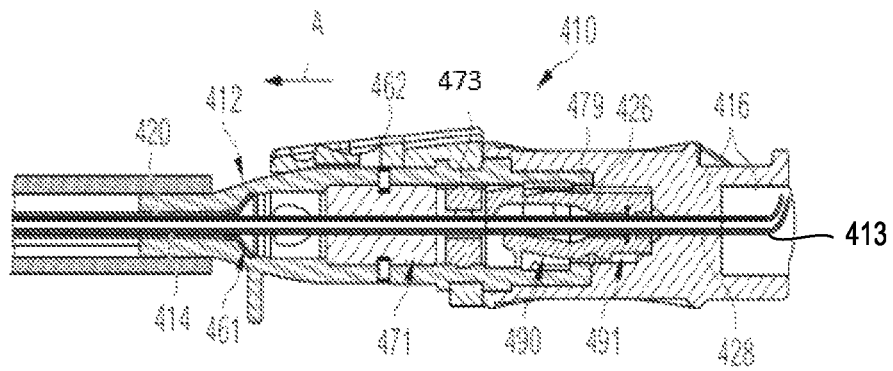

In another embodiment, as shown in FIGS. 13A & 13B the intravenous catheter assembly 410 of the invention comprises a catheter hub 412 arranged at a proximal end 424 of a catheter tube 414 and defining a housing 448; a needle 420 defining an axial direction A and having a needle tip 454 at the distal end of needle 420, and a needle feature 413 at the proximal end of needle 420, wherein the needle 420 extends through the housing 448 and the catheter tube 414 when in a ready position; a needle guard 426 slidably arranged on the needle 420 and partly received in the housing 448 of the catheter hub 412 when the needle is in its ready position. Needle feature 413 may be defined by a curved or bent portion of the proximal end of needle 420. As shown, the needle guard 426 is movably arranged on the needle shaft 28 and an upper end 490 of the needle guard 426 is securely retained in the housing 448 of the catheter hub 412 exposing the lower end 491 of the needle guard 426. In the ready to use position, the entire catheter hub 412 portion with the lower end 491 of the needle guard 426 is securely retained in an inner space 479 of the needle hub 416. The needle hub 416 is provided with inner space 479 defining a housing to movably receive the catheter hub 412 and the lower end 491 of the needle guard 426. The housing 479 of the needle hub 416 has a substantially cylindrical shape, which is structurally beneficial to the provision of rotation capabilities.

In order to enable the catheter hub 412 to securely fit within the housing 479 of the needle hub 416, an inner wall 455 of the needle hub 416 housing 479 is provided with at least one projection 480 and/or groove 481 or vice versa matching with said at least one projection 480 and/or groove 481 is provided in an outer wall of the catheter hub 412. Thus, the catheter hub 412 is safely secured within the needle hub 416 housing 479 by the means of change in dimensions. Alternative arrangements by way of replacing the change of dimensions within the housing 479 and outer wall of catheter hub 412 can also be employed.

For example, both the catheter hub 412 can be snap-fitted in the housing 479 of the needle hub 416. The snap-fit may be formed by a protrusion ring 484 and a corresponding groove ring 485. The protrusion ring 484 may comprise at least one groove and the groove ring 485 may comprise at least one projection or vice versa. The ring of both the projections or groove can be a continuous ring or a spaced apart formation. Other ways and means for a secure engagement are also encompassed.

As shown in FIG. 10B, the needle guard 426 includes a base portion 444 and first 440 and second 442 arms extending from the base portion 444, wherein the first arm 440 is deflected radially outwards by the needle 420 against a restoring force when the needle 420 is in its ready position whereby the needle guard 426 is brought into retaining contact with the catheter hub 412 by retaining mechanisms for retaining the needle guard 426 in the catheter housing 448 as long as the first arm 440 is in its deflected state. The base portion 444 has an axial through-bore 499 for receiving the needle 420. The inner diameter of the bore 499 has a close fit ratio with the outer diameter of the needle 420. The retaining mechanisms include a first disc-like retaining protrusion 493 provided on the first arm 440 and a retaining depression 494 formed in the inner surface of the catheter hub 412 and adapted to receive the retaining protrusion 493.

The disc-like retaining protrusion 493 has the benefit that in the ready position it is in engagement along a circular contact surface with the corresponding retaining depression 494 formed in the inner surface of the catheter hub 412. This provides an engagement between the needle guard 426 and the catheter hub 412 along a substantial annular portion of the retaining protrusion 493 and the retaining depression 494 which provides a safe and reliable engagement between the two components as long as the needle guard 426 is in its ready position and is to be prevented from being retracted out of the needle hub 416. Even if the needle guard 426 is rotated within the catheter hub 412, this secure engagement between the catheter hub 412 and the needle guard 426 holds the needle guard 426 safely within the catheter hub 412.

Because of a depression 494 being formed in the inner surface of the catheter hub 412 for retaining the needle guard 426 in particularly the upper end 490 of the needle guard 426 in the housing 448, instead of e.g. a protrusion, the catheter hub 412 can be manufactured more easily and, thus, at less manufacturing cost, in particular if the catheter hub 412 is a plastic part and e.g. formed by injection molding. At the same time the particular design of the first retaining protrusion 493 provided on the needle guard 426 ensures effective engagement of the retaining protrusion 493 with the retaining depression 494 and, thus, reliable retaining of the needle guard 426 in the catheter hub 412. Hence, the risk of premature release of the needle guard 426 from the catheter hub 412 during withdrawal of the needle 420 from the catheter hub 412 and, thus, the risk of accidental pricking by the needle 420 is reduced.

In one embodiment, the retaining protrusion 493 is of part-circular, in particular semi-circular shape. More specifically, the retaining protrusion 493 may have generally parallel proximal and distal faces and/or a convex, in particular part-cylindrical, peripheral surface.

According to another embodiment, the first retaining protrusion 493 is arranged in the region of a distal end 417 of the first arm 440. According to yet another embodiment, a second disk-like retaining protrusion 495 is arranged on the second arm 442 and adapted to engage with the retaining depression 494 as long as the first arm 440 is in its deflected state. According to yet another embodiment, the second arm 442 can be deflected along its entire length radially inwards when the needle tip 454 is received between the arms 440, 442, to thereby allow the second retaining protrusion 495 to disengage from the retaining depression 494.

According to yet another embodiment, the second retaining protrusion 495 is arranged in the region of a distal end of the second arm 442. In particular, the second retaining protrusion 495 may be arranged opposite from the first retaining protrusion 493. According to yet another embodiment, the retaining depression 494 is an at least part-annular depression, preferably an annular depression.

To explain further, the first arm 440 of the needle guard 426 is longer than the second arm 442 and has a massive distal wall 418 having an undercut for catching the needle tip 454. The distal wall 418 is arranged at a distal end 417 of the first arm 440 and extends in a direction transverse to an axial direction A of the needle 420 such that the distal wall 418 completely blocks the needle 420. The distal wall 418 ensures that the needle tip 454 is prevented from axially projecting out or sideways projecting out of the needle guard 426. The distal wall 418 has a bigger dimension than the distal surface of the second arm 442 and much bigger dimension than the outer diameter of the needle 420 such that the distal wall 418 completely covers and blocks the needle tip 454 once confined and entrapped within the needle guard 426. The first and second arms 440, 442 of the needle guard 426 extend generally in the axial direction A from a distal side 460 of the base portion 444, i.e. generally parallel to the needle shaft 428.

In the ready position, the first arm 440 deflects outward of the needle guard 426 such that the distal wall 418 of the first arm 440 is supported on the needle shaft 428. Further, in this ready position, the first and second arms 440, 442 do not engage or interact with an inner wall/surface of the housing 448 prior and during venipuncture of a patient. This non-contact of the first and second arms 440, 442 with the inner surface of the housing 448 significantly decreases the withdrawal force required and friction caused when a needle 420 is withdrawn through a catheter hub 412 being protected by a needle guard 426 after use.

Upon withdrawal of the needle 420 from the catheter tube 414 and catheter hub 412 the needle shaft 428 moves relative to the needle guard 426 while the needle guard 426 is retained in the catheter hub 412 until the needle tip 454 is received in the needle guard 426. Once the needle tip is received in the needle guard 426 the enlargement 496 of the needle shaft 428 engages with the base portion 444 of the needle guard 426 via a stopping element 438 such that the needle guard 426 can be pulled out of the catheter hub 412 together with the needle 420. An axial movement of the needle 420 relative to the needle guard 426 is now limited, as the distal wall 418 blocks the needle tip 454 axially and the engagement between the enlargement 496 and the base portion 444 via the stopping element 438 prevents the needle tip 454 from being removed via the base portion 444, i.e. the needle tip 454 is safely surrounded by the needle guard 426.

The needle 420 comprises an engagement mechanism provided at a distance from the needle tip 454 for engaging with the needle guard 426 and preventing the needle guard 426 from sliding off the needle 420. Preferably, the engagement mechanism is formed by enlargement 496 of the radial dimension of the needle 420 in at least one direction as compared with a principal profile of the needle 420. The engagement mechanism can be found by a local crimp, a shoulder, a bulge formed as an annular widening etc.

As mentioned above, the needle guard 426 comprises a stopping element 438 engaging with the engagement mechanism of the needle 420 when the needle tip 454 is received between the first 440 and second 442 arms. Preferably, the stopping element 438 defines an axial bore having a cross-section adapted to the principal profile of the needle 420 but being smaller than the enlargement 496 of the needle 420. Furthermore, the stopping element 438 may be made of a material different from the material of the base portion 444, in particular of a metal material. The stopping element 438 may be of disc-like shape or tubular shape and/or arranged on a distal side 460 of the base portion 444. It can be fixed in the base portion 444 or supported in a floating manner on the needle 420.

The catheter assembly 410 is particularly inexpensive to manufacture if the base portion 444, the first and second arms 440, 442 of the needle guard 426 are integrally made from a first material. The first material may, for example, be a plastic material. Thus, the base portion 444, the first and second arms 440, 442 could be manufactured by injection molding.

Alternatively, the base portion 444, and one of the first and second arms 440, 442 could be integrally made from a first material, e.g. a plastic material, and the other one of the first and second arms 440, 442 could be made from a second material different from said first material. For example, said other one of the first and second arms 440, 442 could include a strip of material having spring-like properties, e.g. a strip of sheet metal, providing the above-mentioned inherent elasticity.

The restoring force is created by at least one of an elastic property of the first arm 440 and an additional tension element 446. The tension element 446, for example, a rubber band or the like, surrounds the first and second arms 440, 442. The tension element 446 at least partly surrounding the arms 440, 442 in a region proximal of the first retaining protrusion 493 or—instead of surrounding the two arms 440, 442—biasing the two arms 440, 442 by a linear biasing action. Alternatively or additionally, the first 440 and second 442 arms can be made of a resilient material having elastic properties.

The construction and shape of the improved intravenous catheter assembly 410 according to the various embodiments of the present disclosure provides a simple configuration. The simple and compact design of the intravenous catheter assembly 410 according to the above disclosure is advantageous in a clinical setting because it smoothens the whole catheterization process thereby reducing injury or discomfort to a patient and provides better blood control features. In addition, such design greatly reduces manufacturing costs and is efficient, effective and simple in its construction and use.

The foregoing construction and relationship of the components is believed to provide a needle guard that has very low drag forces, such that the tactile and audible sensations thereof are acceptable to the medical practitioner, while at the same time providing reliable protection of tip thereby minimizing risk of accidental needle sticks therefrom.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth in the claims.

Accordingly, it is not intended that the scope of the foregoing description be limited to the description set forth above, but rather that such description be construed as encompassing such features that reside in the present invention, including all the features and embodiments that would be treated as equivalents thereof by those skilled in the relevant art.

Thus, it is intended that the scope of the present invention herein disclosed should not be limited by the particular disclosed embodiments described above but should be determined only by a fair reading of the appended claims.

LIST OF REFERENCE NUMERALS 110 medical apparatus
212 hub
212b first part of hub
212a second part of hub
114 catheter tube
116 needle hub
218 distal wall
220 needle
122 distal end
124 proximal end
226 needle guard
228 needle shaft
130 needle tip
132 enlargement
233 depression
234 distal section
135 opening
136 proximal section
238 stopper 240 first arm
142 second arm
144 base portion
246 tension element
248 housing
150 distal end section
152 proximal end section
254 chamber
256 inner surface/wall
158 ports
160 handle in needle hub
262 fluid passage
264 protrusion
166 depression
168 opening/window
270 distal radially outer portion
272 passageway
174 stepped surface of 212b
176 stepped surface of 212a
X Axial direction
280 neck
282 wings
284 projection
286 groove
288 annular ring
300 opening in the neck
410 intravenous catheter assembly
411a first fluid path
411b second fluid path
412 catheter hub
412a first part of catheter hub
412b second part of catheter hub
414 catheter tube
416 needle hub
418 distal wall
420 needle
422 distal end
424 proximal end
426 needle guard
428 needle shaft
436 proximal section
438 stopping element
440 first arm
442 second arm
444 base portion
446 tension element
448 housing
450 distal end section
452 proximal end section
454 needle tip
456 inner surface/wall
457 stepped surface of part 12a
458 outer wall/surface
459 stepped surface of part 12b
460 distal side
461 slip ring
462 wings
463 distal section
464 port/port body
465 port opening/inlet
466 bore of the port
467 inner space of catheter housing
468 opening of the catheter housing
469 port/side port
470 sidewall of catheter housing
471 first valve
472 slit
473 second valve
474 blood control septum of second valve
475 plug
476 chamber
477 opening of the catheter housing
478 needle guard casing
479 inner space/housing of needle hub
480 projection
481 groove
482 upper part
483 lower part
484 protrusion ring
485 ring groove
486 top portion
487 bottom portion
488 bore of needle guard casing
489 fitment
490 upper end of needle guard
491 lower end of needle guard
493 first disc like retaining protrusion
494 retaining depression
495 second disc like retaining protrusion
496 enlargement
497 opening
498 local depression
499 through-bore
A axial direction

The invention claimed is:

1. An intravenous catheter assembly comprising:
a catheter tube;
a catheter hub having a distal end and a proximal end, wherein the distal end is joined to the catheter tube and the proximal end defines a housing having an inner space;
a needle extending through the catheter hub and the catheter tube and defining an axial direction, wherein the needle has opposite proximal and distal ends, the distal end forming a needle tip;
a needle hub attached to the proximal end of the needle having a housing;
a needle guard comprising an upper end and a lower end; wherein the needle guard is arranged on the needle wherein the upper end of the needle guard is securely retained in the housing of the catheter hub exposing the lower end of the needle guard and wherein in a ready to use position of the intravenous catheter assembly, a catheter hub portion with the lower end of the needle guard is securely retained in an inner space of the needle hub; and
a first valve and a second valve provided in the inner space in the catheter hub, wherein the second valve comprises at least one of a groove, a channel, or a suitable projection formed on an outer surface of the second valve, wherein the outer surface of the second valve is configured to compatibly sit within at least one of a groove, a channel or a projection formed on an inner surface of the catheter hub; and wherein the second valve is configured with a plug also being housed in the inner space in the catheter hub.

2. The intravenous catheter assembly as claimed in claim 1, wherein the needle hub housing comprises an inner wall; wherein the inner wall of the needle hub housing comprises at least one selected from the group consisting of a projection and a groove; wherein the catheter hub comprises an outer wall; and wherein the at least one selected from the group consisting of the projection and the groove of the inner wall matches with at least one selected from the group consisting of a projection and a groove of the outer wall.

3. The intravenous catheter assembly as claimed in claim 1, wherein the needle guard comprises a base portion and first and second arms extending from the base portion, wherein the first arm is deflected radially outwards by the needle against a restoring force when the needle is in its ready position whereby the needle guard is brought into retaining contact with the catheter hub by retaining mechanisms for retaining the needle guard in the catheter housing as long as the first arm is in its deflected state and wherein the retaining mechanisms comprise a first disc-like retaining protrusion provided on the first arm and a retaining depression formed in an inner surface of the catheter hub and adapted to receive the retaining protrusion.

4. The intravenous catheter assembly as claimed in claim 1, wherein the needle guard is un-slidably arranged on the needle and the needle guard is completely retained in an enclosed inner space of the needle hub.

5. The intravenous catheter assembly as claimed in claim 1, wherein the needle guard is slidably arranged on the needle and the needle guard is partially retained in an inner space of the needle hub.

6. The intravenous catheter assembly as claimed in claim 1, wherein the needle hub housing comprises a holding mechanism for holding the needle guard against retracting forces; wherein the needle hub defines an inner circumferential surface; wherein the needle guard defines an outer surface and the outer surface comprises at least one or more selected from the group consisting of a depression and a protrusion; wherein the holding mechanism comprises at least one or more selected from the group consisting of a depression and a protrusion formed on the inner circumferential surface of the hub adapted to engage the at least one or more protrusions or depressions formed on the outer surface of the needle guard.

7. The intravenous catheter assembly as claimed in claim 1, wherein the needle defines an enlargement; and an opening arranged distally or proximally from the enlargement; and wherein the opening extends in an axial direction for a distance of approximately 0.5 mm.

8. The intravenous catheter assembly as claimed in claim 1, wherein the needle hub comprises a handle; and wherein the handle of the needle hub has different anti-slip devices on its surface; wherein the anti-slip devices comprise at least one selected from the group consisting of an indentation and a protrusion.

9. The intravenous catheter assembly as claimed in claim 1, wherein the proximal end of the needle comprises a needle feature.

10. The intravenous catheter assembly as claimed in claim 9, wherein the needle feature comprises a needle bend.

11. The intravenous catheter assembly as claimed in claim 9, wherein the needle feature increases a force required to separate the needle from the needle hub.

12. The intravenous catheter assembly as claimed in claim 1, wherein the catheter hub comprises a first part with a distal end section and a second part with a proximal end section defining the catheter hub housing and wherein the distal end section of the first part is joined with the proximal end section of the second part in a fluid tight manner by complementary end portions.

13. The intravenous catheter assembly as claimed in claim 1, wherein the second valve is disk shaped.

14. The intravenous catheter assembly as claimed in claim 1, wherein the second valve is arranged proximate the first valve.

15. The intravenous catheter assembly as claimed in claim 14, wherein the second valve is configured to hold the first valve in its position.

16. The intravenous catheter assembly as claimed in claim 1, wherein the second valve and an interior surface of the catheter hub comprise cooperating alignment features.

17. The intravenous catheter assembly as claimed in claim 16, wherein the cooperating alignment features comprise at least one projection and at least one groove and wherein the at least one groove is structured to match the at least one projection.

18. The intravenous catheter assembly as claimed in claim 16, wherein the cooperating alignment features comprise the second valve comprising at least one projection and the interior surface of the catheter hub comprising at least one groove and wherein the at least one groove is structured to match the at least one projection.

19. The intravenous catheter assembly as claimed in claim 16, wherein the cooperating alignment features comprise the second valve comprising at least one groove and the interior surface of the catheter hub comprising at least one projection and wherein the at least one groove is structured to match the at least one projection.

* * * * *